United States Patent
Sato et al.

(10) Patent No.: US 7,758,602 B2
(45) Date of Patent: Jul. 20, 2010

(54) LANCING DEVICE, METHOD OF MAKING LANCING DEVICE, PUMP MECHANISM, AND SUCKING DEVICE

(75) Inventors: Yoshiharu Sato, Kyoto (JP); Etsuo Hirao, Kyoto (JP); Masahiro Fukuzawa, Kyoto (JP); Takatoshi Uchigaki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 705 days.

(21) Appl. No.: 11/523,160

(22) Filed: Sep. 19, 2006

(65) Prior Publication Data

US 2007/0016239 A1    Jan. 18, 2007

Related U.S. Application Data

(63) Continuation of application No. 10/466,146, filed as application No. PCT/JP02/00165 on Jan. 11, 2002, now Pat. No. 7,131,984.

(30) Foreign Application Priority Data

| Jan. 12, 2001 | (JP) | ................................. 2001-4962 |
| Jul. 26, 2001 | (JP) | ............................. 2001-225687 |
| Nov. 21, 2001 | (JP) | ............................. 2001-356515 |

(51) Int. Cl.
A61B 17/14    (2006.01)

(52) U.S. Cl. ....................................... 606/182; 606/181

(58) Field of Classification Search ....................... None
See application file for complete search history.

(56) References Cited

U.S. PATENT DOCUMENTS 5,662,127 A    9/1997  De Vaughn

| 5,666,966 A | | 9/1997 | Horie et al. |
| 5,873,887 A | * | 2/1999 | King et al. .................. 606/182 |
| 5,916,230 A | | 6/1999 | Brenneman et al. |
| 6,152,942 A | | 11/2000 | Brenneman et al. |

FOREIGN PATENT DOCUMENTS

| JP | 6-327655 | 11/1994 |
| JP | 08-164122 | 6/1996 |
| JP | 11-9577 | 1/1999 |
| JP | 2000-225110 | 8/2000 |
| WO | WO 98/24366 | 6/1998 |

OTHER PUBLICATIONS

Japanese Office Action from the corresponding JP 2002-555693, mailed Mar. 4, 2008.

\* cited by examiner

*Primary Examiner*—Corrine M McDermott
*Assistant Examiner*—Christopher D Prone
(74) *Attorney, Agent, or Firm*—Hamre, Schumann, Mueller & Larson, P.C.

(57) ABSTRACT

A lancing device according to the present invention includes: a housing; a moving body movable relatively to the housing for forward movement of a needle; a driving mechanism for forward movement of the moving body; a hollow pressing portion at a front end of the housing for contact with a part where a puncture is to be made; and a pump mechanism capable of causing a vacuum to act inside the pressing portion. The pump mechanism is capable of adjusting the vacuum. The pump mechanism includes for example: a moving portion capable of reciprocating in a first direction and a second direction away from the first direction. Preferably, the adjustment of the vacuum is made by changing the number of reciprocations of the moving part in the first and the second directions.

7 Claims, 30 Drawing Sheets

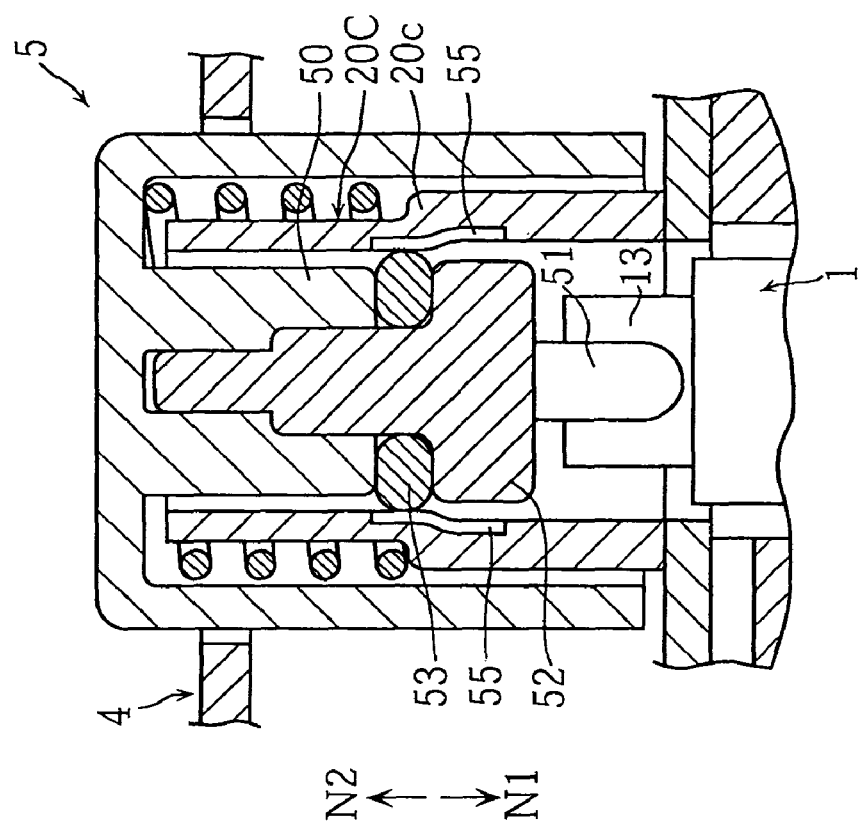
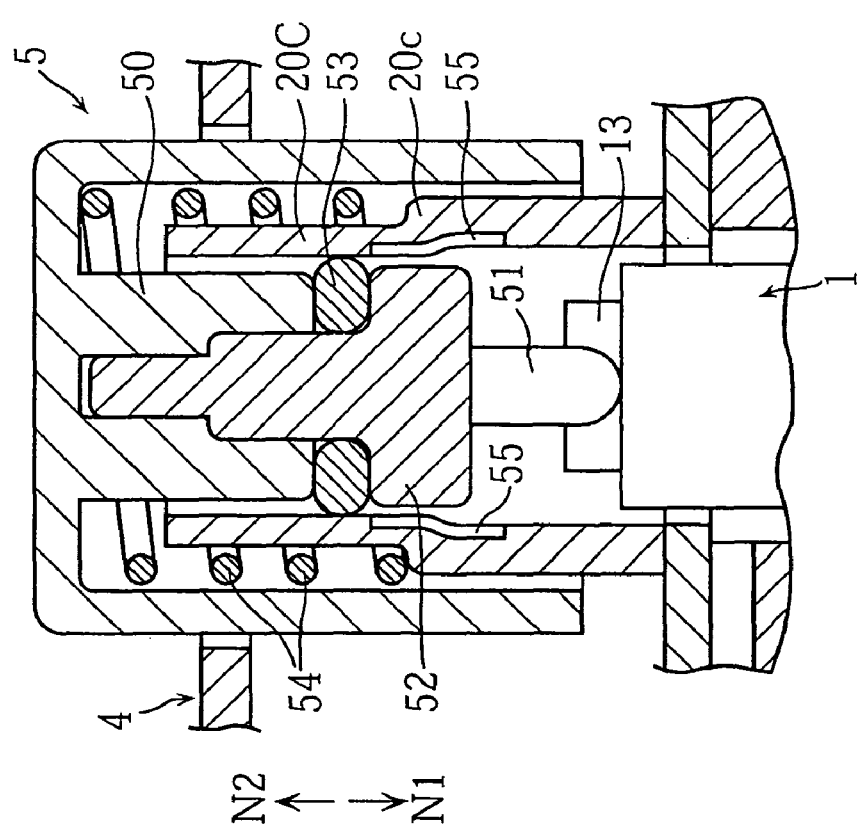

[Embodiment 1] : V3=0.72597cm³

[Embodiment 2] : V3=1.45194cm³

[Embodiment 3] : V3=2.1779cm³

FIG.20A
FIG.20B
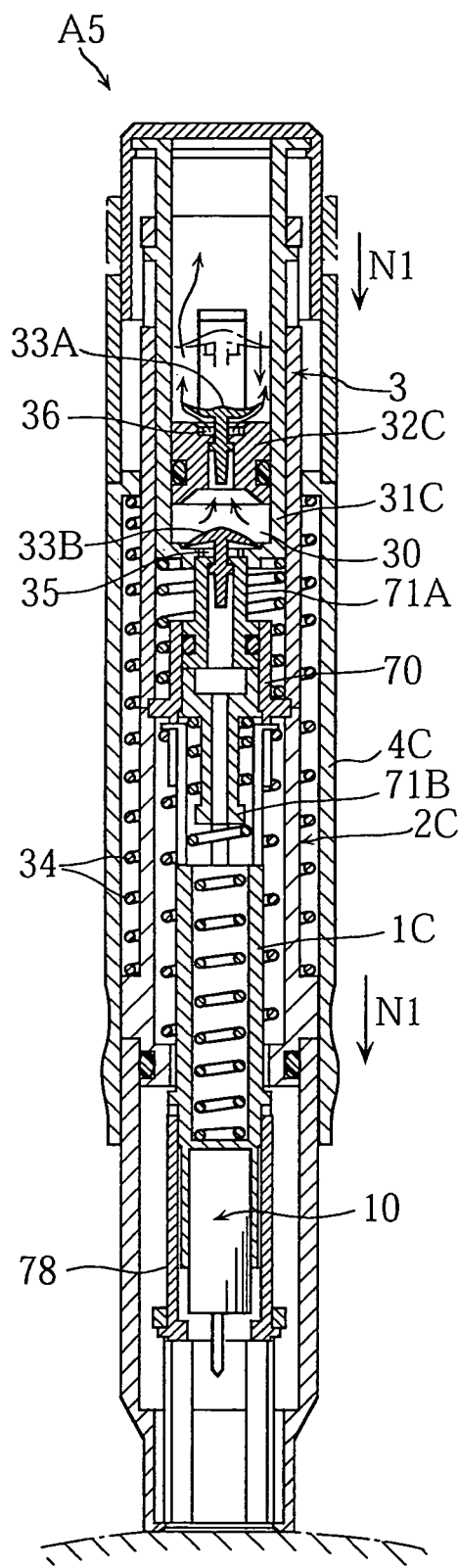
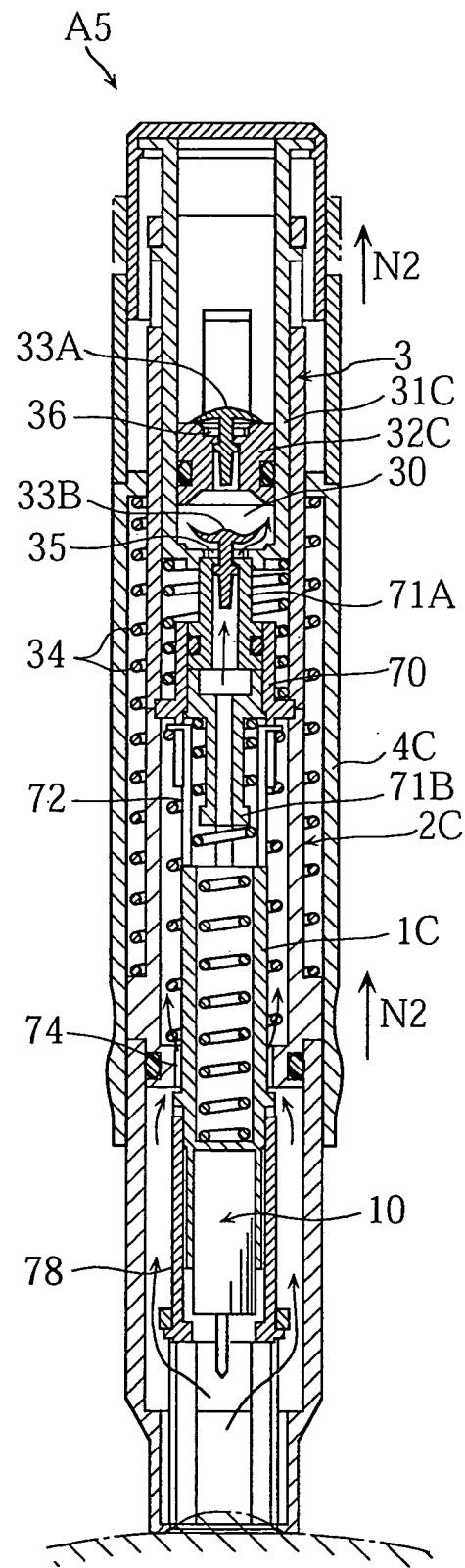

LANCING DEVICE, METHOD OF MAKING LANCING DEVICE, PUMP MECHANISM, AND SUCKING DEVICE

This application is a Continuation of application Ser. No. 10/466,146, filed Jul. 11, 2003 which is a National Stage application of PCT/JP02/00165, filed Jan. 11, 2002.

TECHNICAL FIELD

The present invention relates to a lancing device used for sticking a needle into the skin when taking test samples of blood, other body fluid or tissues, and to a method of manufacturing the lancing device.

The present invention further relates to a pump mechanism suitable for creating a vacuum on the skin, and to a sucking device for sucking on the skin.

BACKGROUND ART

Conventionally, a lancing device of this kind is disclosed in the Japanese Patent Laid-Open No. 11-9577 for example. The lancing device disclosed in this gazette includes, as shown in FIG. 31 of this application, a generally tubular housing 90 and a lancet holder 92 holding a lancet L. The housing 90 has an end fitted with a tubular plunger 93 having a check valve 91. Though details will not be described here, according to this lancing device, when the plunger 93 is pushed in a direction shown by an arrow Na, the lancet holder 92 latched at a predetermined place in the housing 90 is forced to unlatch. Thus, the lancet holder 92 is propelled forward by an elastic force from a spring 95 toward an open front end 90a of the housing 90. Though not illustrated, the front end of the housing 90 is pressed onto the skin, and therefore the forward movement of the lancet holder 92 drives the tip of the lancet L into the skin.

Once the lancet holder 92 has moved forward, the lancet holder 92 is returned by an elastic force from a return spring 94. Likewise, the plunger 93 is moved back to its original position by an elastic force from a spring 96. This causes a volume increase in a space 97 in the plunger 93, creating a vacuum in the housing 90. A vacuum can also be created in the housing 90 by returning action of members 98a, 98b. Therefore, if the front end of the housing 90 is still pressed on the skin, the skin comes under the vacuum, and bleeding is promoted from the place pricked by the lancet L. The check valve 91 closes when the plunger 93 returns, thereby helping the generation of the vacuum, and opens when the plunger 93 is moved forward, to help smoothen the forward movement of the plunger 93.

However, the conventional lancing device has following drawbacks.

Specifically, there is personal difference in the volume of bleeding from the place pricked by the lancet L. Also, the same person bleeds differently from place to place; some place bleed easily while some others do not. However, conventionally, the level of vacuum created in the housing 90 is more or less the same all the time. Therefore, from time to time depending on the vacuum in the housing 90, it is not possible to obtain a sufficient amount of bleeding, or the lancing causes too much bleeding.

Another problem is that conventionally, the vacuum can be created in the housing 90 only after the lancet L has been shot to the skin. On the other hand, when lancing is to be made on a thin and easily relaxing part of the skin for example, it is sometimes more preferable that the a vacuum should be created first to suck on the skin, before shooting the lancet L. However, this is not available in the convention, and has been an issue of inconvenience some times.

Further, users of lancing devices are often clinical patients or the aged who do not have physical or bodily advantages. Therefore, the devices should preferably be very easy to use.

DISCLOSURE OF THE INVENTION

A first aspect of the present invention provides a lancing device incorporating a vacuum generating mechanism, comprising: a housing; a moving body movable relatively to the housing for forward movement of a needle; a driving mechanism for forward movement of the moving body; a hollow pressing portion at a front end of the housing for contact with a part where a puncture is to be made; and a pump mechanism capable of causing a vacuum to act inside the pressing portion. The pump mechanism is capable of adjusting the vacuum.

Preferably, the pump mechanism includes: a moving portion capable of reciprocating in a first direction and a second direction away from the first direction; and a pressure chamber having a volumetric capacity varied by the reciprocation of the moving portion.

It is preferable that the adjustment of the vacuum is made by changing the number of reciprocations of the moving part in the first and the second directions.

The pump mechanism includes for example: a cylinder and a plunger collectively providing a pressure chamber capable of communicating with an outside of the pressing portion via a discharge port and capable of communicating with an inside of the pressing portion via an intake port; an operating mechanism operated by another action than for the driving mechanism, for causing one of the plunger and the cylinder to reciprocate relatively to the other; a first check valve capable of opening and closing the discharge port, opening the discharge port when the volumetric capacity of the pressure chamber decreases; and a second check valve capable of opening and closing the intake port, opening the intake port when the volumetric capacity of the pressure chamber increases.

In this case, the discharge port and the first check valve are provided in the cylinder or in the plunger for example.

Preferably, vacuum generation by the pump mechanism is selectable from whichever of before and after the moving body is moved forward.

The pressure chamber, which must be communicatable with the inside of the pressing portion, may be provided outside or inside the housing.

Preferably, the pump mechanism further includes an elastic force generating portion storing an elastic force generated by the movement of the moving portion in the first direction and moving the moving portion in the second direction by releasing the elastic force. The vacuum is generated by the movement of the moving portion in the first direction.

Preferably, the driving mechanism includes: a first engaging portion provided in the moving body; an elastic portion for forward movement of the moving body, for urging the moving body in the forward direction; a second engaging portion for engagement with the first engaging portion, for latching the moving body in the housing; a lancing operation member having at least a part thereof exposed to outside of the housing; and an unlatching portion to act on the engagement between the first and the second engaging portions thereby unlatching the moving body upon operation of the lancing operation member.

Preferably, the pressure chamber is provided by a cylinder and a plunger, communicatable with an outside of the housing via a discharge port, and communicatable with an inside of the pressing portion via an intake port. The cylinder is movable relatively to the housing, and the unlatching action by the unlatching portion to the moving body is actuated by direct or indirect pushing by the cylinder on the unlatching portion.

The unlatching portion may be fixed to the lancing operation member.

The cylinder is fitted reciprocatably in the housing for example.

Preferably, in the lancing device according to the present invention, the inside of the pressing portion communicates with an outside of the housing when the lancing operation member is operated further, after the moving member is unlatched.

It is preferable that the lancing operation member is operable under a smaller resistance before the unlatching of the moving member than after.

Preferably, the lancing device according to the present invention further comprises a pressure reducing operation member for movement of the moving portion.

The pressure reducing operation member reciprocates with respect to the housing for example, and preferably the pressing portion is rotated axially thereof by the reciprocating action of the pressure reducing operation member with respect to the housing.

Preferably, the lancing device according to the present invention further comprises an elastic portion urging the moving portion for returning reverse movement. The elastic portion is provided outside of the pressure chamber.

The second engaging portion is provided, for example, in a latching member fixed to the housing and providing a housing space for the moving body, the elastic portion for forward movement and the elastic portion for reverse movement.

It is preferable that the drive mechanism further comprises an elastic portion for reverse movement of the moving body, in series with the elastic portion for forward movement of the moving body, for supplying the moving body with a reverse moving force after the forward movement of the moving body.

A second aspect of the present invention provides a lancing device comprising: a housing; a moving body movable relatively to the housing for forward movement of a needle; and a driving mechanism for forward movement of the moving body. The driving mechanism includes: an elastic portion for forward movement for supplying the moving body with a forward moving force; a first engaging portion in the moving body; and a second engaging portion engagable with the first engaging portion and provided in the housing. In addition, the device further comprises an elastic portion for reverse movement of the moving body placed in series with the elastic portion for forward movement, for supplying the moving body with a reverse moving force after the forward movement of the moving body.

The second engaging portion is provided, for example, in a latching member fixed to the housing and providing a housing space for the moving body, the elastic portion for forward movement and the elastic portion for reverse movement.

The elastic portion for forward movement and the elastic portion for rearward movement are fixed to the latching member while being housed in the housing space, for example. With this arrangement, the elastic portions are elastically expanded or compressed by the forward and reverse movement of the moving body.

A third aspect of the present invention provides a lancing device incorporating a vacuum generating mechanism, comprising: a housing; a moving body movable relatively to the housing for forward, movement of a needle; a driving mecha-nism for forward movement of the moving body; a hollow pressing portion at a front end of the housing for contact with a part where a puncture is to be made; and a pump mechanism capable of causing a vacuum to act inside the pressing portion. The pump mechanism includes: a moving portion capable of reciprocating in a first direction and a second direction away from the first direction; and an elastic force generating portion storing an elastic force by the movement of the moving portion in the first direction and moving the moving portion in the second direction by releasing the elastic force. The vacuum is generated by the movement of the moving portion in the first direction.

A fourth aspect of the present invention provides a method of making a lancing device comprising: a housing; a moving body movable relatively to the housing for forward movement of a needle; a driving mechanism for forward movement of the moving body; a hollow pressing portion at a front end of the housing for contact with a part where a puncture is to be made; a pressure chamber having a volumetric capacity varied by the reciprocation of the moving portion; and a pump mechanism capable of causing a vacuum to act inside the pressing portion. The pump mechanism is capable of adjusting the vacuum. A maximum vacuum to be generated inside the pressing portion is adjusted by selecting at least one of: a volumetric capacity of the pressure chamber when there is no outer force acting on the moving portion; and a maximum volumetric capacity increase possible in the pressure chamber when there is an outer force acting on the moving portion.

A fifth aspect of the present invention provides a method of making a lancing device comprising: a housing; a moving body movable relatively to the housing for forward movement of a needle; a driving mechanism for forward movement of the moving body; a hollow pressing portion at a front end of the housing for contact with a part where a puncture is to be made; a pressure chamber having a volumetric capacity varied by the reciprocation of the moving portion; and a pump mechanism capable of causing a vacuum to act inside the pressing portion. The pump mechanism is capable of adjusting the vacuum. The number of reciprocations to be made by the moving portion before approaching a maximum vacuum to be generated inside the pressing portion is adjusted by selecting an actual volumetric capacity of the housing.

A sixth aspect of the present invention provides a pump mechanism having a pressure chamber for generation of a vacuum in a vacuum generation chamber, comprising: a moving portion capable of reciprocating in a first direction and a second direction away from the first direction; and an elastic force generating portion storing an elastic force by the movement of the moving portion in the first direction and moving the moving portion in the second direction by releasing the elastic force. The vacuum is generated by the movement of the moving portion in the first direction.

A seventh aspect of the present invention provides a sucking device comprising a pump mechanism for sucking a target place by generation of a vacuum in a vacuum generation chamber. The pump mechanism is capable of adjusting the vacuum.

The pump mechanism includes for example, a moving portion capable of reciprocating in a first direction and a second direction away from the first direction, and a pressure chamber having a volumetric capacity varied by the reciprocation of the moving portion. The adjustment of the vacuum is made by changing the number of reciprocations of the moving part in the first and the second directions.

The pump mechanism further includes for example, an elastic force generating portion storing an elastic force by the movement of the moving portion in the first direction and moving the moving portion in the second direction by releasing the elastic force. With this arrangement, the vacuum is generated by the movement of the moving portion in the first direction.

BRIEF DESCRIPTION OF THE DRAWINGS

FIG. 4A and FIG. 4B are sectional views showing an arrangement around an operative cap.

FIG. 20A and FIG. 20B are sectional views for describing a pressure reducing operation in the lancing device in FIG. 15 through FIG. 17.

BEST MODE FOR CARRYING OUT THE INVENTION

Figure 1:
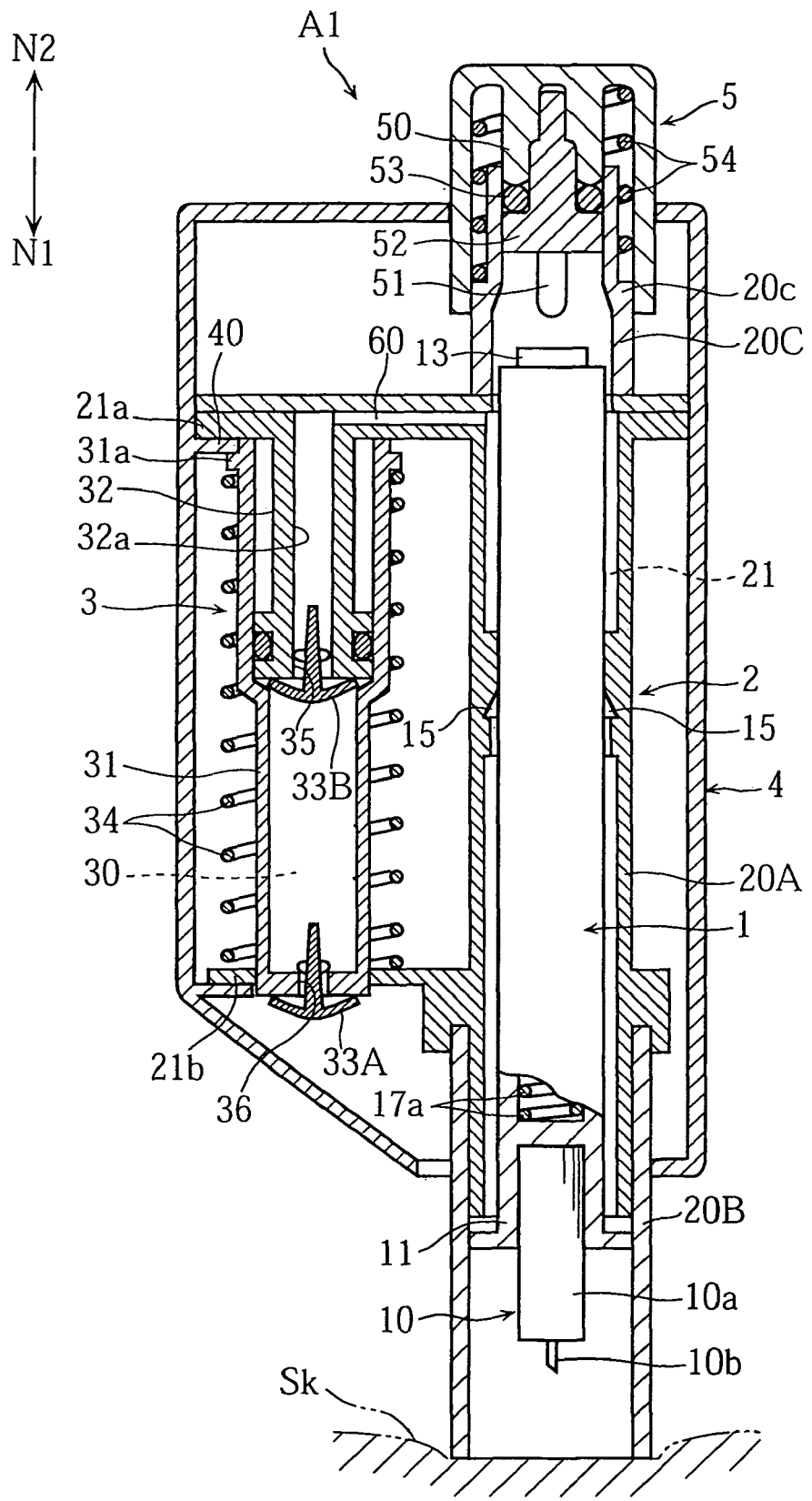
FIG. 1 is a sectional view of a lancing device according to a first embodiment of the present invention.

A lancing device having a vacuum creating capacity according to the present invention will be described with reference to FIG. 1 through FIG. 10.

As clearly shown in FIG. 1, a lancing device A1 according to the present embodiment comprises a lancet holder 1 for holding a lancet 10, a housing 2 for incorporating the lancet holder 1, a pump mechanism 3, an operative casing 4 for driving the pump mechanism 3, an operative cap 5 for moving forward the lancet holder 1, and the parts and members to be described below.

The lancet 10 includes, for example, a main body 10a made of synthetic resin and a metal needle 10b projecting out of a front end face of the main body.

The housing 2 includes a first through a third tubular portions 20A, 20B, 20C. The housing 2 includes a space 21 for housing the lancet holder 1 and allowing it to reciprocate. As will be described later, when lancing with the lancing device A1, a front end of the second tubular portions 20B is pressed onto a skin Sk to which the lancing is to be made. Since the second tubular portions 20B can be accidentally contaminated by the body fluid being sampled, the second tubular portions 20B can be made detachable from the first tubular portions 20A to allow replacement in a way that it can be fitted and removed like a cap. The housing 20A can be formed either of a single material, or of a combination of plural materials.

The operative casing 4 is for driving the pump mechanism 3, and is tubular, surrounding the housing 2 and the pump mechanism 3. The operative casing 4 can be reciprocated longitudinally of the housing 2, in directions indicated by arrows N1, N2.

Figure 5:
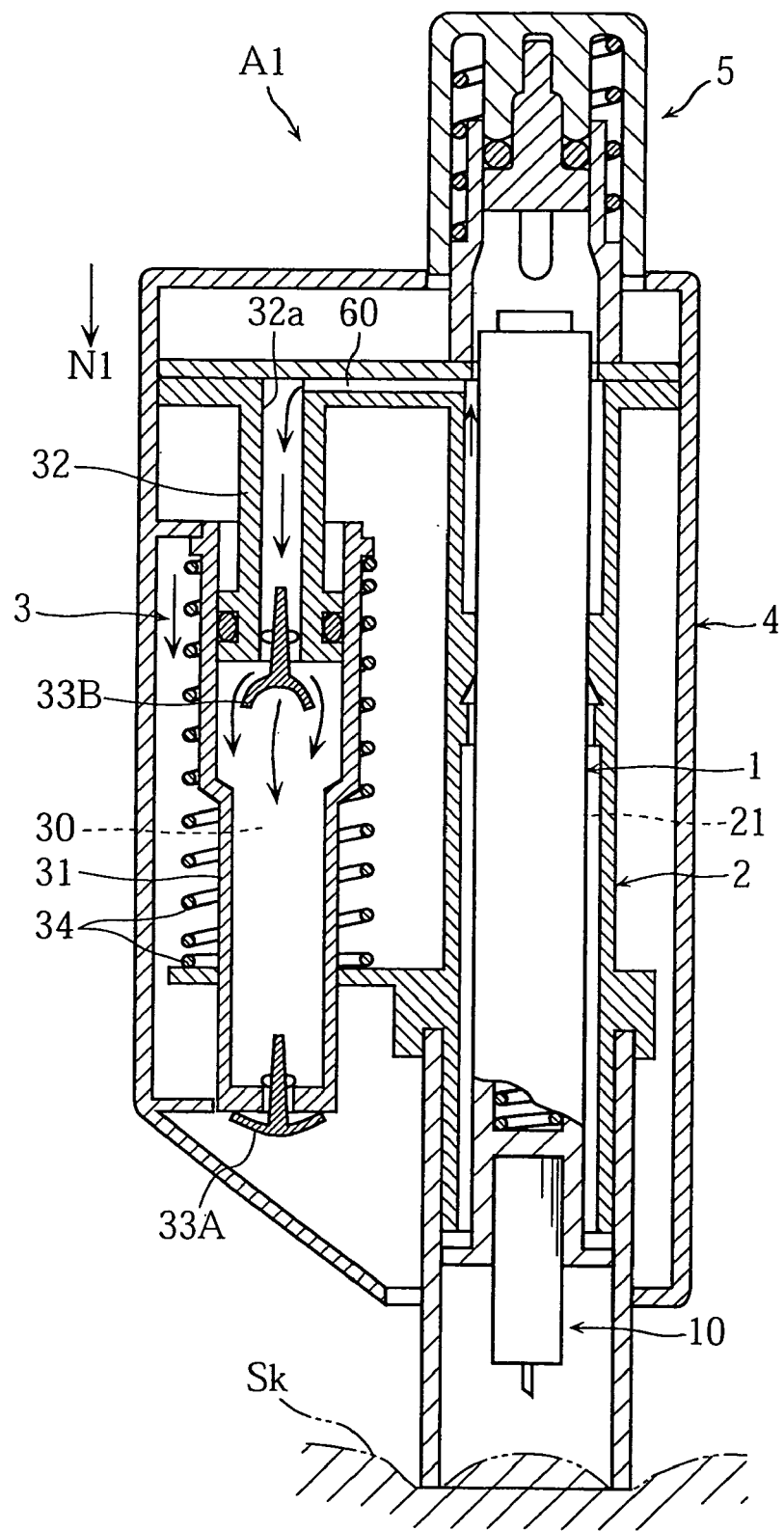
FIG. 5 is a sectional view for describing a pressure reducing operation in the lancing device in FIG. 1.

The pump mechanism 3 includes a cylinder 31 formed with a pressure chamber 30 therein, a plunger 32 slidably fitted into the cylinder 31, a first check valve 33A, a second check valve 33B; and a return spring 34. The plunger 32 is formed integrally with a first support 21a which projects out of the first tubular portions 20A from the housing 2. The plunger 32 may of course be formed separately from the housing 20 and fixed to the first tubular portions 20A. On the other hand, the cylinder 31 can reciprocate in the directions N1, N2 relatively to the housing 2 and the plunger 32. The cylinder 31 has a base end (the upper end in the diagram) formed with a flange 31a engaged by a projection 40 of the operative casing 4. Thus, as shown in FIG. 5, when operation is made to move the operative casing 4 downwardly in the direction N1, the cylinder 31 comes down together, increasing the capacity of the pressure chamber 30.

The return spring 34 is provided by e.g. a compression coil spring, and placed between a second support 21b which projects out of the first tubular portions 20A of the housing 2 and a flange 31a of the cylinder 31. When the cylinder 31 moves forward or downward along with the operative casing 4 in the direction N1, the return spring 34 is compressed between the flange 31a and the second support 21b, storing a predetermined amount of elastic force to raise the cylinder 31 and the operative casing 4.

The first check valve 33A opens and closes an air discharge port 36 formed on the front end of the cylinder 31, allowing the air in the pressure chamber 30 to be discharged through the air discharge port 36 and out of the pressure chamber 30, but blocking the reverse airflow. The plunger 32 is hollow, having a through hole 32a. The plunger 32 has a front end formed with an air intake port 35. The second check valve 33B opens and closes the air intake port 35, allowing the air to come through the through hole 32a of the plunger 32 into the pressure chamber 30, but blocking the reverse airflow. The through hole 32a communicates with the space 21 of the housing 2 via an air passage 60 formed between the base end of the plunger 32 and the first support plate 21a of the housing 2. In the space 21, the air passage 60 communicates with an open front end of the housing 2, making it possible as will be described later that when a vacuum is created in the pressure chamber 30 of the pump mechanism 3, the created vacuum acts on the open front end of the housing 2.

Figure 2:
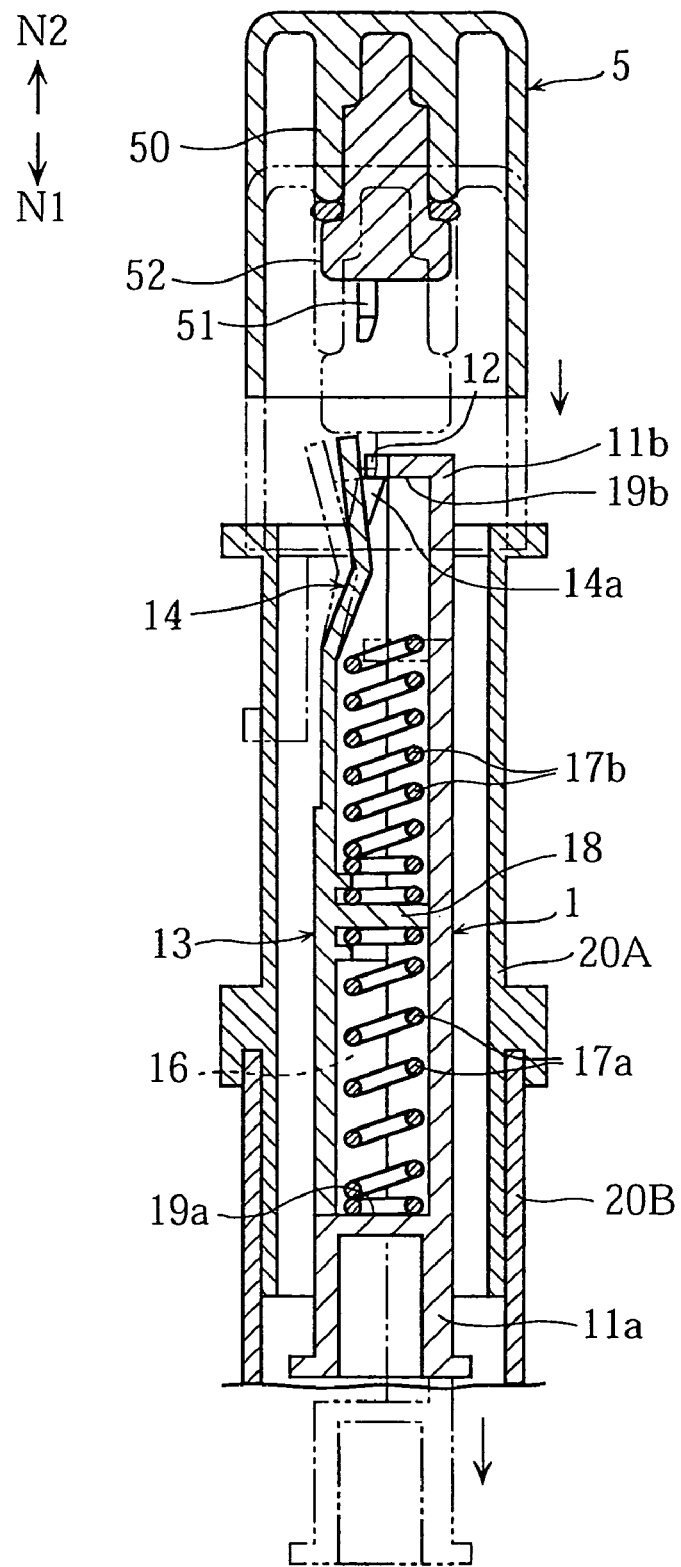
FIG. 2 is a sectional view of a primary portion for describing a lancing mechanism.
Figure 3:
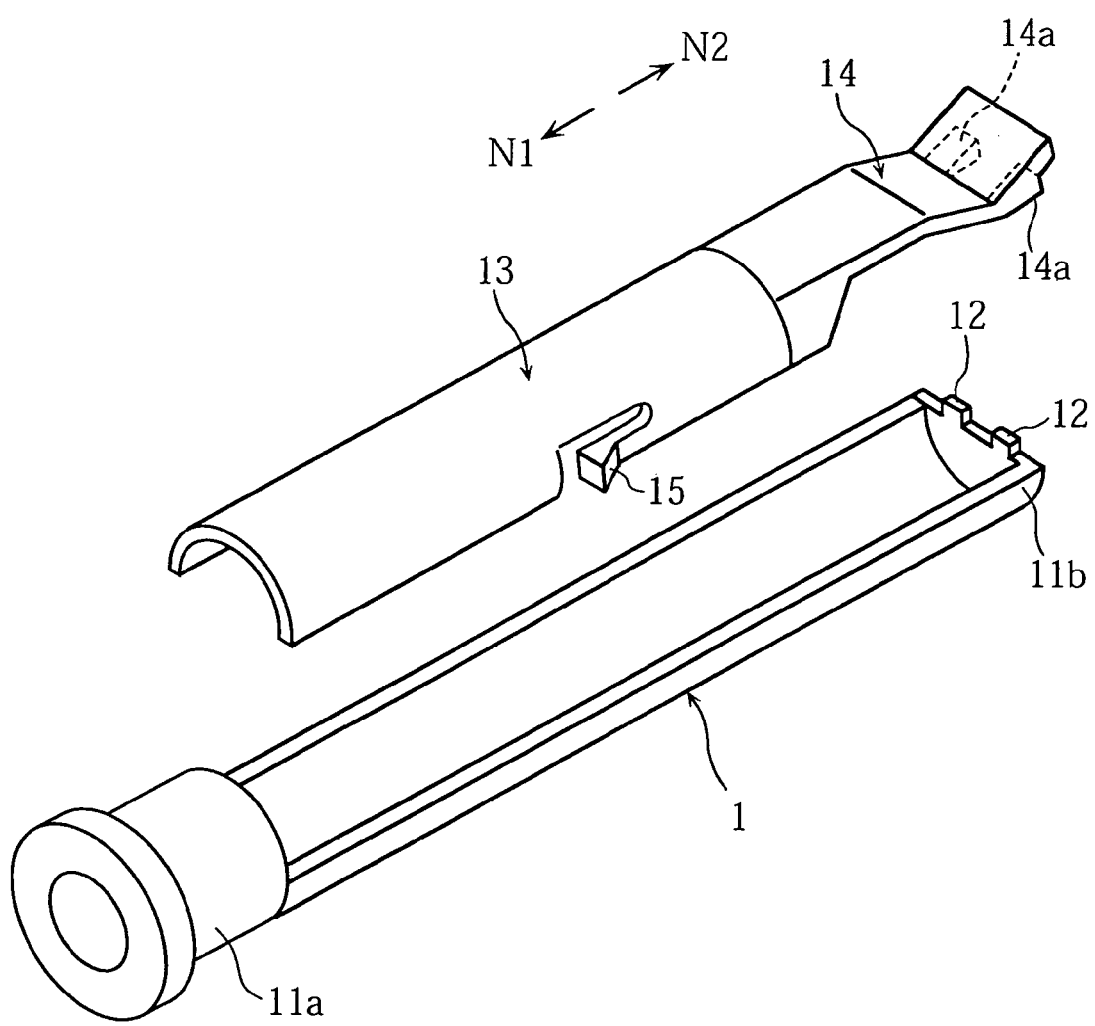
FIG. 3 is a perspective view of a lancet holder and a latching tab.

As shown in FIG. 1 through 3, the lancet holder 1 is a structure elongated in the directions N1, N2. The lancet holder 1 can be engaged with a latching member 13 thereby urged ahead, and can be released ahead (in the direction N1 in FIG. 1 through FIG. 3) when disengaged by a pressing operation on the operative cap 5. The lancet holder 1 as a hole is like a half pipe. The lancet holder 1 has a tubular tip 11a, in which the lancet 10 is held. The lancet holder 1 has another end 11b formed with a pair of projections 12. These projections 12 represent the first engaging portion.

The latching member 13 also is a structure elongated in the directions N1, N2. The latching member 13 has an end formed with a second engaging portion 14. The second engaging portion 14 works as a leaf spring, and is formed with a pair of engaging projections 14a. These engaging projections 14a are engaged by the pair of projections 12. The latching member 13 has an intermediate portion formed with an engaging piece 15 for fixing the latching member 13 in the housing 2.

The latching member 13 provides a housing space 16 together with the lancet holder 1. The housing space 16 houses coil springs 17a, 17b in series. These coil springs 17a, 17b each has an end fixed to a fixture 18 formed on the latching member 13. The coil springs 17a, 17b each have another end, on the other hand, which are free with respect to the latching member 13 but can interfere with walls 19a, 19b of the lancet holder 1.

Once the pair of projections 12 are engaged with the pair of engaging projections 14a, the coil spring 17a comes under compression in the housing space 16, storing an elastic force for propelling the lancet holder 1 forward. It should be noted here that the engagement of the pair of engaging projections 12 with the pair of engaging projections 14a can be achieved by pressing the lancet holder 1 into the housing 2 from the front toward the base end. When the lancet holder 1 is unlatched, the elastic force of the coil spring 17a shoots the lancet holder 1 in the direction N1. The forward movement of the lancet holder 1 in the direction N1 compresses the coil spring 17b. Therefore, after the lancet holder 1 has made a predetermined amount of forward movement in the direction N1, the elastic force from the coil spring 17a presses back the lancet holder 1 by a predetermined amount, pulling the needle 10b out of the skin Sk. The coil springs 17a, 17b can of course be replaced by alternatives such as bellow-like spring, sponge and rubber foam.

According to the lancing device A1, the coil spring 17a for supplying the lancet holder with the forward force and the coil spring 17b for supplying the returning force are placed in line. This makes size reduction possible around the lancing mechanism compared to a parallel placement design of the coil springs. Further, compared to a design in which the coil springs are placed around the lancet holder, the spring inner diameter can be smaller, and there is no need for providing a space for the coil springs around the lancet holder. As a result, it becomes possible to reduce the volume around the lancing mechanism, and reduce the volume of air to be pumped out by the pump mechanism 3. Thus, it becomes possible to reduce the size of the pump mechanism 3 without undue sacrifice, or it becomes possible to create a high level of vacuum to act on the skin.

The operative cap 5 is fitted into the operative casing 4 around the third tubular portions 20C of the housing 2, slidably with respect to the housing 2. The operative cap 5 includes a fixed portion 50 and an unlatching member 52 having a projection 51. An O ring 53 is placed between the fixed portion 50 and the unlatching member 52. This maintains air tightness in the housing 2, and allows the operative cap 5 to move in the directions N1, N2 with respect to the housing 2 (the third tubular portions 20C). The operative cap 5 houses a coil spring 54 fitted around the third tubular portions 20C. The coil spring 54 has a lower end fixed to a step 20c of the third tubular portions 20C. Thus, when the operative cap 5 is pressed in the direction N1, the operative cap 5 is moved down while pressing the coil spring 54. During this, when the operative cap 5 has moved down over a predetermined distance, the unlatching member 52 acts on the engagement between the pair of projections 12 and the pair of engaging projections 14a, and unlatches the lancet holder 1. On the other hand, when the pressing force on the operative cap 5 is removed, the coil spring 54 moves the operative cap 5 in the direction N2, to the original position.

As shown in FIG. 4A and FIG. 4B, the third tubular portion 20C is formed with a recess 55 for allowing the air to pass through. When the operative cap 5 is above the latch releasing position, the O ring 53 is above the recess 55. On the other hand, when the operative cap 5 is slightly below the latch releasing position, the O ring 53 is at the level of the recess 55. Thus, when the operative cap 5 is pressed down further (in the direction N1), the recess 55 allows the air to flow from the outside into the housing 2, canceling the vacuum in the housing 2.

Next, a use example and function of the lancing device A1 will be described.

First, if it is preferable to put the skin Sk under a vacuum before the lancet 10 is pushed into the skin Sk, as shown in FIG. 5, the operative casing 4 is pressed in the direction N1 relatively to the housing 2 while the front end of the housing 2 is held onto the skin Sk. In this operation, the cylinder 31 moves down relatively to the plunger 32, increasing the capacity of the pressure chamber 30 thereby creating a vacuum in the pressure chamber 30, which causes the second check valve 33B to open. Then, the air in the space 21 of the housing 2 flows into the pressure chamber 30 through the air passage 60 and the through hole 32a, creating a vacuum in the housing 2, which acts on the skin Sk.

Figure 6:
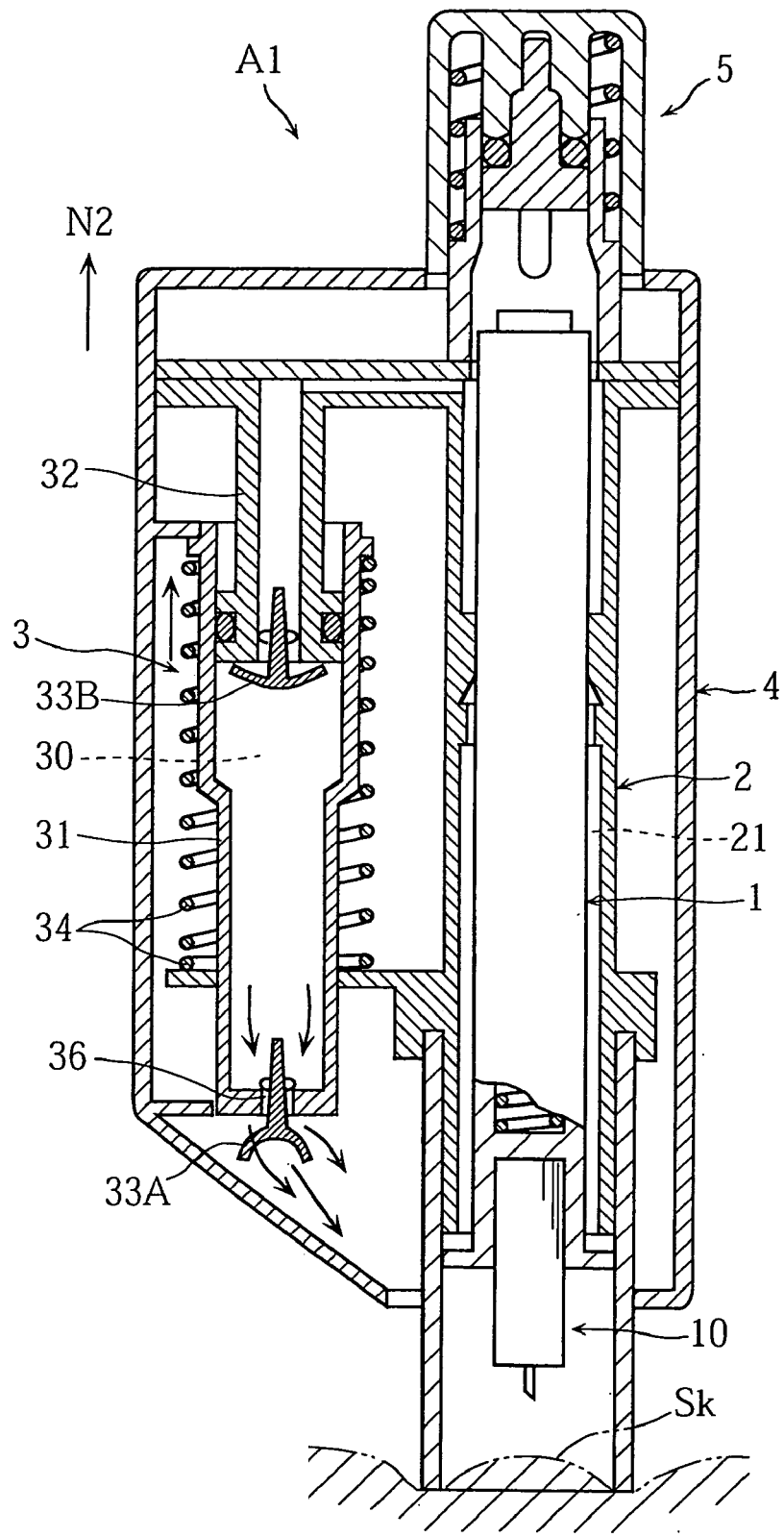
FIG. 6 is a sectional view for describing the pressure reducing operation in the lancing device in FIG. 1.

After the operative casing 4 has been pressed down, it is easy to let the operative casing 4 and the cylinder 31 move back to their original positions using the elastic force from the spring 34. As shown in FIG. 6, when the operative casing 4 and the cylinder 31 are raised back in the direction N2, the capacity of the pressure chamber 30 decreases, causing the second check valve 33B to close and the first check valve 33A to open. Thus, when the cylinder 31 is moved back to the original position, it is possible to let the air in the pressure chamber 30 escape appropriately through the air discharge port 36 while maintaining the vacuum in the space 21 of the housing 2.

As described, if a vacuum in the space 21 of the housing 2 can be maintained when the operative casing 4 and the cylinder 31 are moved back to their original positions, it becomes possible when the operative casing 4 is further pressed down again, to increase the level of vacuum in the space 21 of the housing 2, thereby increasing the negative pressure (decrease the absolute air pressure value) in the space 21. As a result, according to the lancing device A, it is possible to appropriately adjust the level of vacuum acting on the skin Sk, by increasing or decreasing the number of pushing operations.

Figure 7:
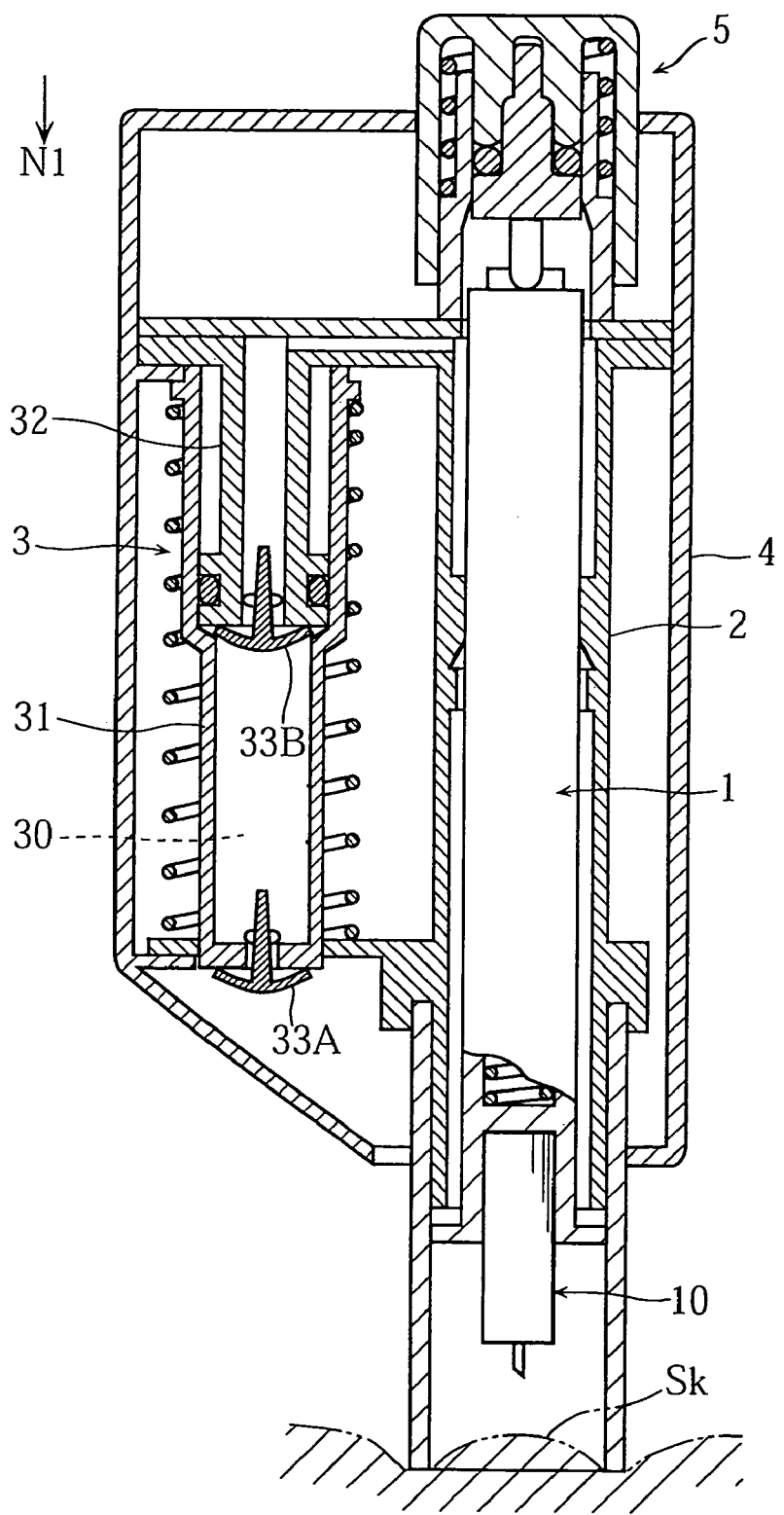
FIG. 7 is a sectional view for describing a lancing operation in the lancing device in FIG. 1.
Figure 8:
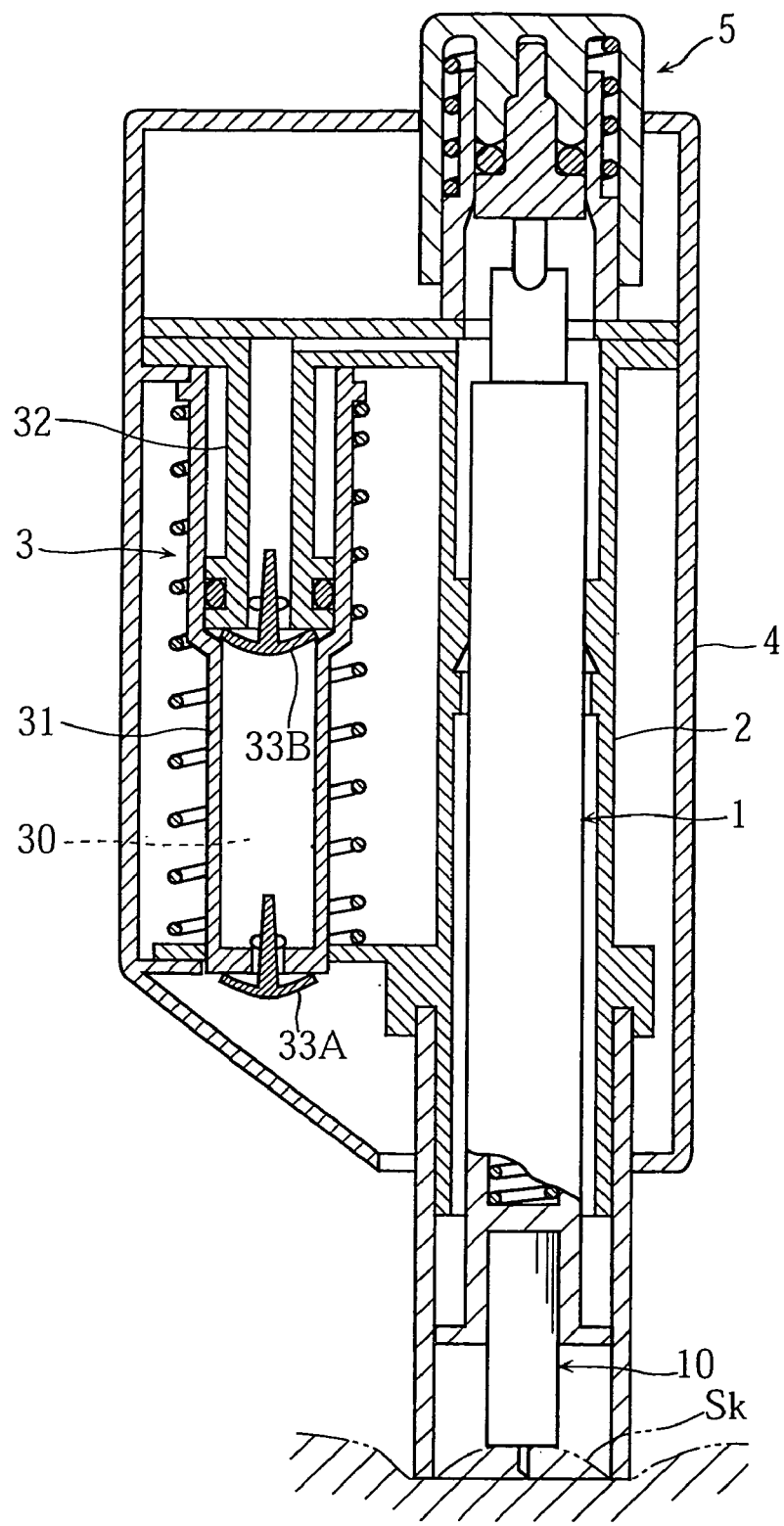
FIG. 8 is a sectional view for describing the lancing operation in the lancing device in FIG. 1.
Figure 9:
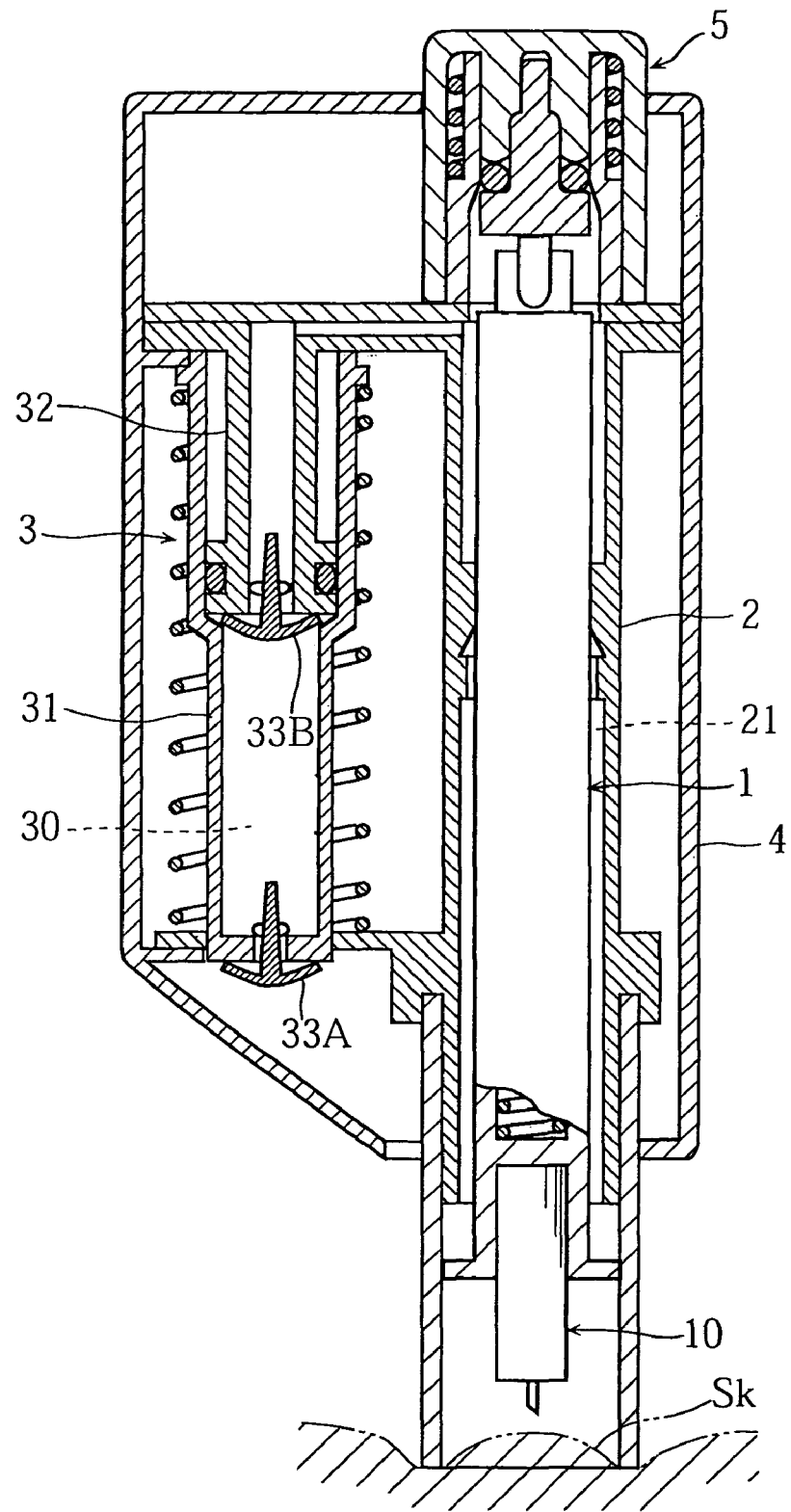
FIG. 9 is a sectional view for describing a vacuum canceling operation in the lancing device in FIG. 1.

Next, in order to drive the lancet 10 into the skin Sk, as shown in FIG. 2 and FIG. 7, the operative cap 5 is pressed down in the direction N1 to release the latch on the lancet holder 1. As shown in FIG. 2 and FIG. 8, this allows the coil spring 17a to move the lancet holder 1 forward, causing the lancet 10 to stick into the skin Sk. Once the lancet 10 is driven into the skin Sk, the spring 17b (See FIG. 2) thrusts the lancet holder 1 back, thereby pulling the lancet 10 out of the skin Sk immediately. Since the skin Sk is under the vacuum created earlier, bleeding is promoted from the place pricked by the lancet 10. This helps bleeding to be a relatively large level while making the depth of lancing by the lancet 10 as small as possible.

As shown in FIG. 4A and FIG. 4B, when the operative cap 5 is further pressed down in the direction N1, the space 21 in the housing 2 communicates with the outside via the recess 55 of the operative cap 5, allowing the air to come inside the space 21 through the recess 55. Thus, the pressure in the space 23 comes back to a normal atmospheric pressure. Such an operation makes very easy to release the housing 2 from the skin Sk.

According to the lancing device A1, the vacuum acting on the skin Sk cannot be released easily unless the operative cap 5 is pressed further after the operative cap 5 is first operated to drive the lancet 10 into the skin Sk. This arrangement makes sure that the vacuum acting on the skin Sk is not mistakenly lost, that the skin Sk is properly bulged and stimulated for improved blood flow before the lancet 10 is driven. Further, both driving of the lancet 10 and releasing of the vacuum can be made continuously by pressing the operative cap 5, resulting in simplified operation of these steps.

According to the use example described above, a vacuum is first created in the space 21 of the housing 2, and then the lancet 10 is driven into the skin Sk. Alternatively, according to the lancing device A1, the steps may be reversed. Namely, the sequence may be that the operative cap 5 is pressed to drive the lancet 10 into the skin first, and then the operative casing 4 is operated to create a vacuum on the place pricked by the lancet 10. This sequence too can promote bleeding from the place pricked by the lancet 10, by means of vacuum. As described, the lancing device A1 is convenient in that the user can select whether the vacuum should be created before or after the lancet 10 is driven into the skin Sk. Further, according to the lancing device A1, when the operative casing 4 is reciprocated in order to create a vacuum, the front end of the housing 2 gives a massage to the skin Sk, potentially resulting in further improvement in the blood flow in the skin Sk.

Figure 10A:
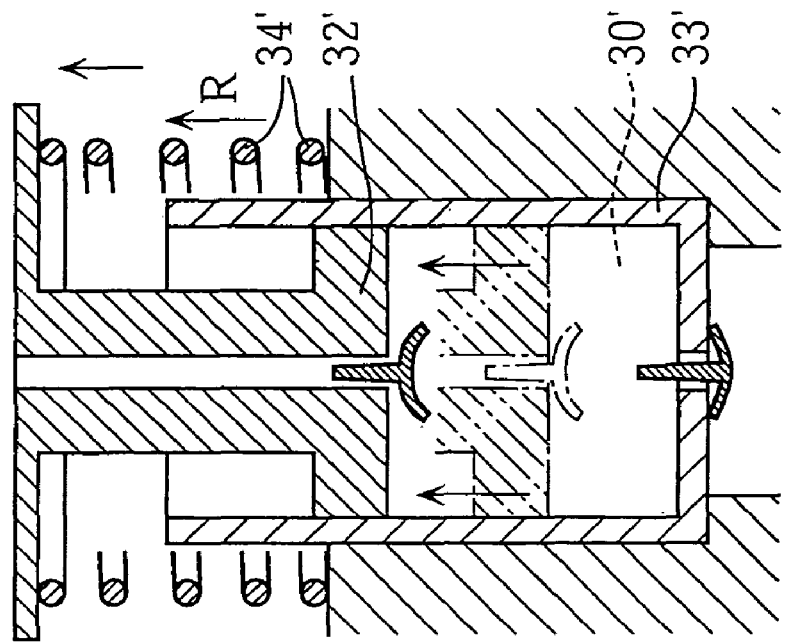
FIG. 10A and FIG. 10B are sectional views of a primary portion for describing a pressure reducing operation in a comparative example.
Figure 10B:
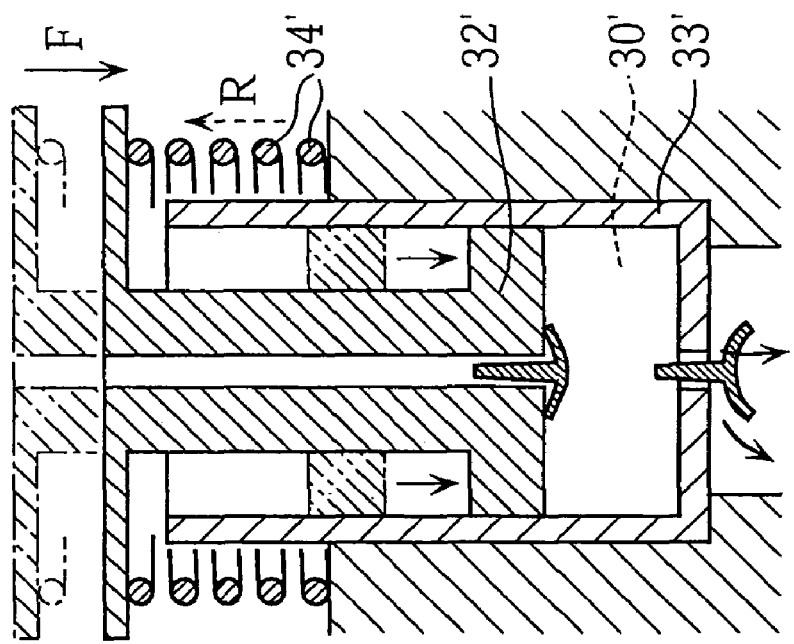

According to the lancing device A1, a vacuum is created when the operative casing 4 is pressed down against the elastic force from the return spring 34. Therefore, the vacuum can be created right away. In addition, there is another advantage as follows: Specifically, the pump mechanism could have been different from the one according to the present embodiment, and can be as shown in FIG. 10A, in which the capacity of a pressure chamber 30' decreases when a plunger 32' is pressed down against an elastic force R from a spring 34'. Thereafter, as shown in FIG. 10b, the capacity of the pressure chamber 30' increases to create a vacuum when the plunger 32' is raised back into the position by the elastic force R of the spring 34'. A challenge in such an arrangement however, is that the elastic force R from the spring 34' must be able to not only raise the plunger 32' against friction between the plunger 32' and the pump mechanism 33' but also overcome the atmospheric pressure in order to create a vacuum in the pressure chamber 30'. In other words, a total of the two forces is required. The force required to press the plunger 32' is greater than the elastic force R of the spring 34'.

On the contrary, according to the arrangement offered by the present embodiment, a vacuum is not created in the pressure chamber 30 when the return spring 34 comes back into the original state after it is compressed. Therefore, the return spring 34 should only be able to provide a force necessary to overcome a friction between the plunger 32 and the cylinder 31 for raising the cylinder 31 back into the original position. Therefore, the return spring 34 according to the present embodiment can have a spring constant smaller than that of the spring 34' shown in FIG. 10A and FIG. 10B. As a result, according to the present embodiment, the amount of force necessary for pressing down the cylinder 31 and the operative casing 4 against the elastic force from the return spring 34 can be accordingly smaller, leading to improved operability.

According to the lancing device A1, the vacuum created in the housing 2 can be adjustable. A maximum level of the vacuum and the number of reciprocations of the operative casing 4 necessary for approaching the set maximum level of vacuum can be selected on the basis of experiment to be described next.

Figure 11A:
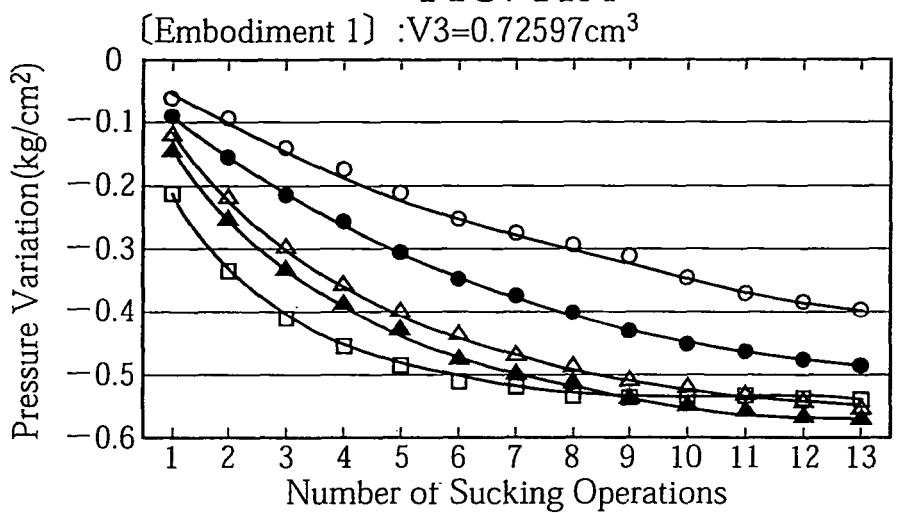
FIG. 11A through FIG. 11C are graphs showing a relationship between the number of sucking actions and vacuum.
Figure 11B:
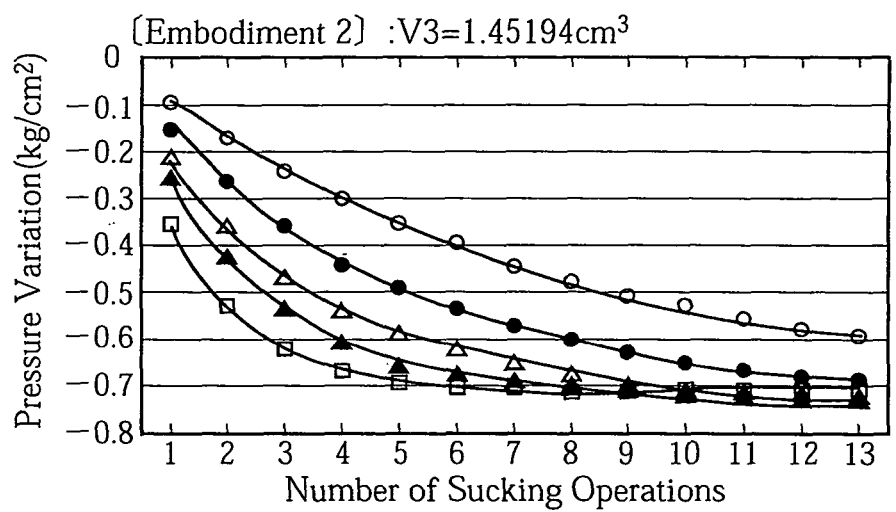
Figure 11C:
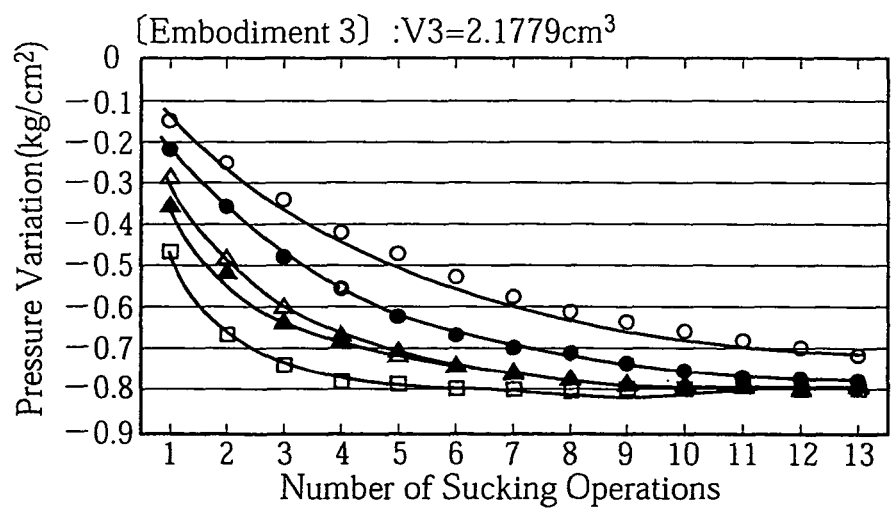

The inventor et al studied a relationship between the number of reciprocations of the operative casing and pressure change in the housing 2. Results of the study are shown in FIG. 11A through FIG. 11C. Each of the graphs shows results of an experiment under different conditions. In the experiment, two values were fixed; dead capacity V2 of the pressure chamber 30 (the volumetric capacity of the pressure chamber 30 under normal conditions), and capacity V3 (a maximum volumetric capacity increase in the pressure chamber 30) obtained by subtracting the dead capacity V2 from a maximum capacity of the pressure chamber 30 achieved. On the other hand, actual volumetric capacity of the housing 2 (i.e. the space occupied by a gaseous body (including however, the space of the air passage 60 shown in FIG. 1, and the through hole 32a of the plunger 32) was varied. V1 through V3 were created in tubular columns of the same diameter, and adjusted in terms of the height. Settings used in each of the first through the third embodiments are shown in the following tables 1 through 3 respectively.

| | | Capacity (cm³) | | |
|---|---|---|---|---|
| | Symbols in the Graphs | V1 (Actual Capacity of Housing) | V2 (Dead Capacity) | V3 (Max Increase in Capacity) |
| Embodiment 1 (FIG. 11A) | ○ | 13.2665 | 0.785 | 0.72597 |
| | ● | 6.63325 | | |
| | △ | 3.97995 | | |
| | ▲ | 2.6533 | | |
| | □ | 1.32665 | | |
| Embodiment 2 | ○ | 13.2665 | 0.785 | 1.45194 |

-continued

| | | Capacity (cm³) | | |
|---|---|---|---|---|
| | Symbols in the Graphs | V1 (Actual Capacity of Housing) | V2 (Dead Capacity) | V3 (Max Increase in Capacity) |
| (FIG. 11B) | ● | 6.63325 | | |
| | △ | 3.97995 | | |
| | ▲ | 2.6533 | | |
| | □ | 1.32665 | | |
| Embodiment 3 (FIG. 11C) | ○ | 13.2665 | 0.785 | 2.1779 |
| | ● | 6.63325 | | |
| | △ | 3.97995 | | |
| | ▲ | 2.6533 | | |
| | □ | 1.32665 | | |

As understood from FIG. 11A through FIG. 11C, the number of sucking operations necessary for approaching the maximum level of vacuum in the housing 2 can be decreased if the actual capacity V1 of the housing 2 is decreased. Further, a common tendency can be understood from all of the graphs. Specifically, the larger the actual capacity V1 of the housing 2, the greater the number of pumping actions will be needed to approach the maximum level of vacuum in the housing 2. In other words, when it is desirable to create a relatively high level of vacuum by a single pumping action, the actual capacity V1 of the housing 2 should be made small. On the other hand, when gradual increase to a target level of vacuum is desirable, the actual capacity V1 of the housing 2 should be made large. If the maximum capacity increase V3 is large, the maximum level of vacuum is large, whereas if the maximum capacity increase V3 of the pressure chamber 30 is small, the maximum level of vacuum is small. Thus, by selecting the maximum capacity increase V3 in the pressure chamber 30, the maximum level of vacuum achievable in the housing 2 can be adjusted. Also, by selecting the actual capacity V1 of the housing 2, the number of pumping actions necessary for approaching the maximum level of vacuum can be adjusted.

It should be noted here however, that the results shown in FIG. 11A through FIG. 11C are those when the dead capacity V2 of the pressure chamber 30 was constant. Thus, it is also possible to adjust the maximum level of vacuum by varying V2 while having V3 fixed.

Figure 12:
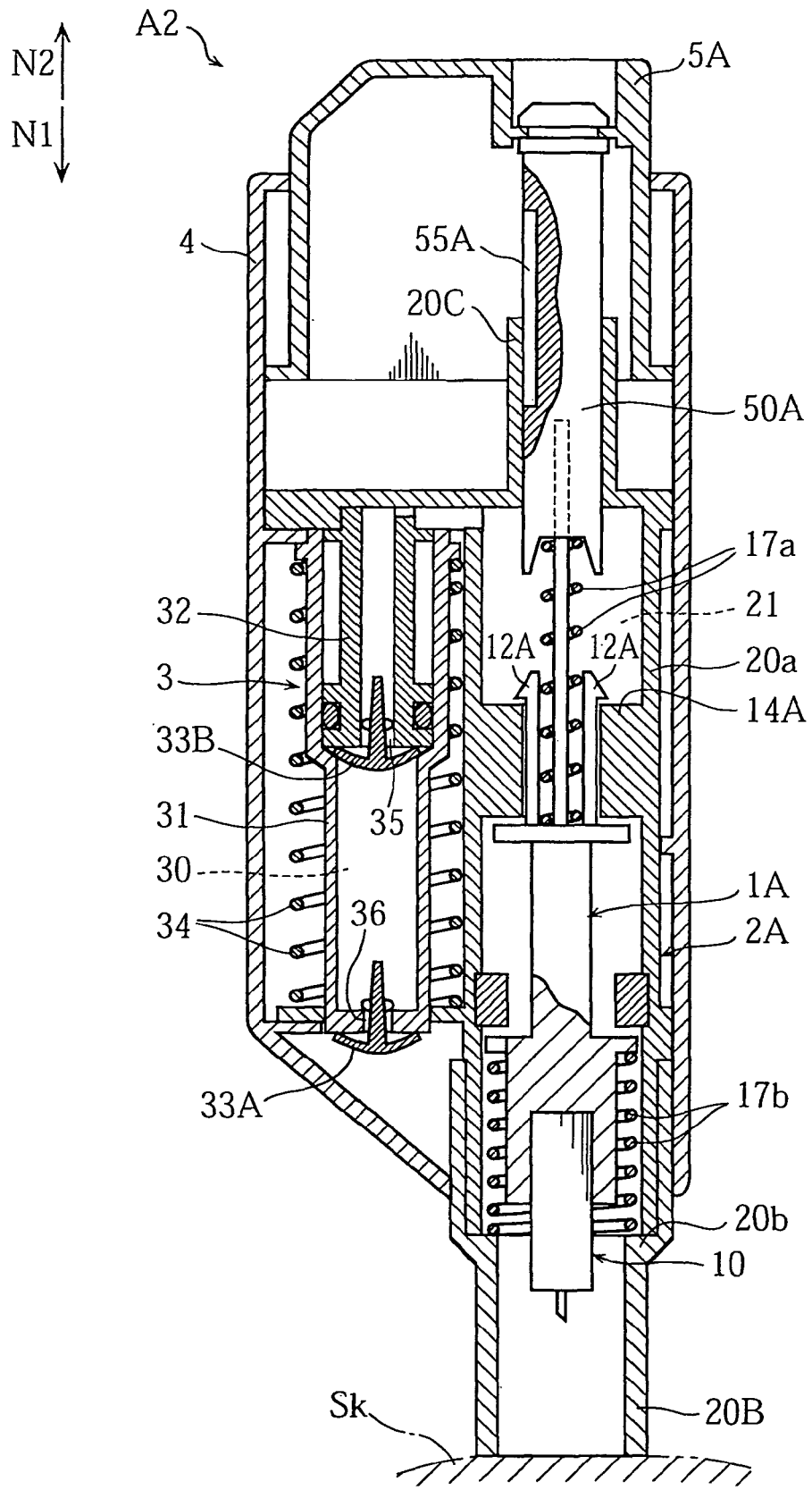
FIG. 12 is a sectional view of a lancing device according to a second embodiment of the present invention.

Next, a lancing device A2 according to a second embodiment of the present invention will be described with reference to FIG. 12. In FIG. 12, members and elements identical with or similar to those in the lancing device A1 described already are given the same alphanumeric codes and their description will not be repeated here.

As shown in FIG. 12, the lancing device A2 has a different lancing mechanism from the one used in the lancing device A1. This lancing mechanism includes a lancet holder 1A, an operative cap 5A, a forward propelling spring 17a and a rearward propelling spring 17b.

In the lancing device A2, the lancet holder 1A includes a plurality of latching pawls 12A. These latching pawls 12A engage with steps 14a in the housing 2A. The engagement with the steps 14A by the latching pawls 12A can be achieved by pushing the lancet holder 1A from the front end side toward the base end side of the housing 2A.

The operative cap 5A is slidably fitted into an operative casing 4. To the operative cap 5A, a push rod (an unlatching portion) 50A is hooked. The push rod 50A is slidably fitted, while maintaining air tightness with respect to the third tubular portions 20C of the housing 2A. The push rod 50A has an outer circumferential wall provided with a recess 55A serving as an air passage. Although the recess 55A can communicate with the outside of the housing 2A, the communication with the space 21 of the housing 2A is not established under normal conditions. However, when the operative cap 5A is pressed by an appropriate amount, the recess 55A opens up in the space 21, establishing the communication with the space 21 via the recess 55A.

The forward propelling spring 17a has an upper end fixed to the push rod 50A and a lower end fixed to the lancet holder 1A. The forward propelling spring 17a is compressed when the latching pawls 12A are engaged with the steps 14a in the housing 2A.

On the other hand, the rearward propelling spring 17b has an upper end fixed to the lancet holder 1A and a lower end fixed to a steps 20b of the housing 2A (the second tubular portions 20B). The spring 17b is compressed when the lancet holder 1A moves forward.

According to the lancing mechanism described above, when the operative cap 5A is pressed in the direction N1, the push rod 50A hooked to the operative cap 5A moves forward while compressing the forward propelling spring 17a, thereby compressing the latching pawls 12A. When pressed by the push rod 50A, the latching pawls 12A are disengaged (unlatched) from the steps 14a. When released from the engagement, the lancet holder 1 is shot forward in the direction N1 by the elastic force from the coil spring 17a. Also, after moving forward by a predetermined amount toward the tip of the housing 2A, the lancet holder 1A is moved back by a predetermined amount by an elastic force from a spring 17b provided in the housing 2A.

When the operative cap 5A is further pressed, the recess 55A of the push rod 50A makes the air passage for the space 21 to communicate with the outside. Therefore, any vacuum which may have been created in the housing 2 by the pump mechanism 3 can be cancelled by pressing the operative cap 5A.

Next, a lancing device A3 according to a third embodiment of the present invention will be described with reference to FIG. 13. In this diagram, members and elements identical with or similar to those in the lancing device A1 and A2 described already are given the same alphanumeric codes and their description will not be repeated here.

Figure 13:
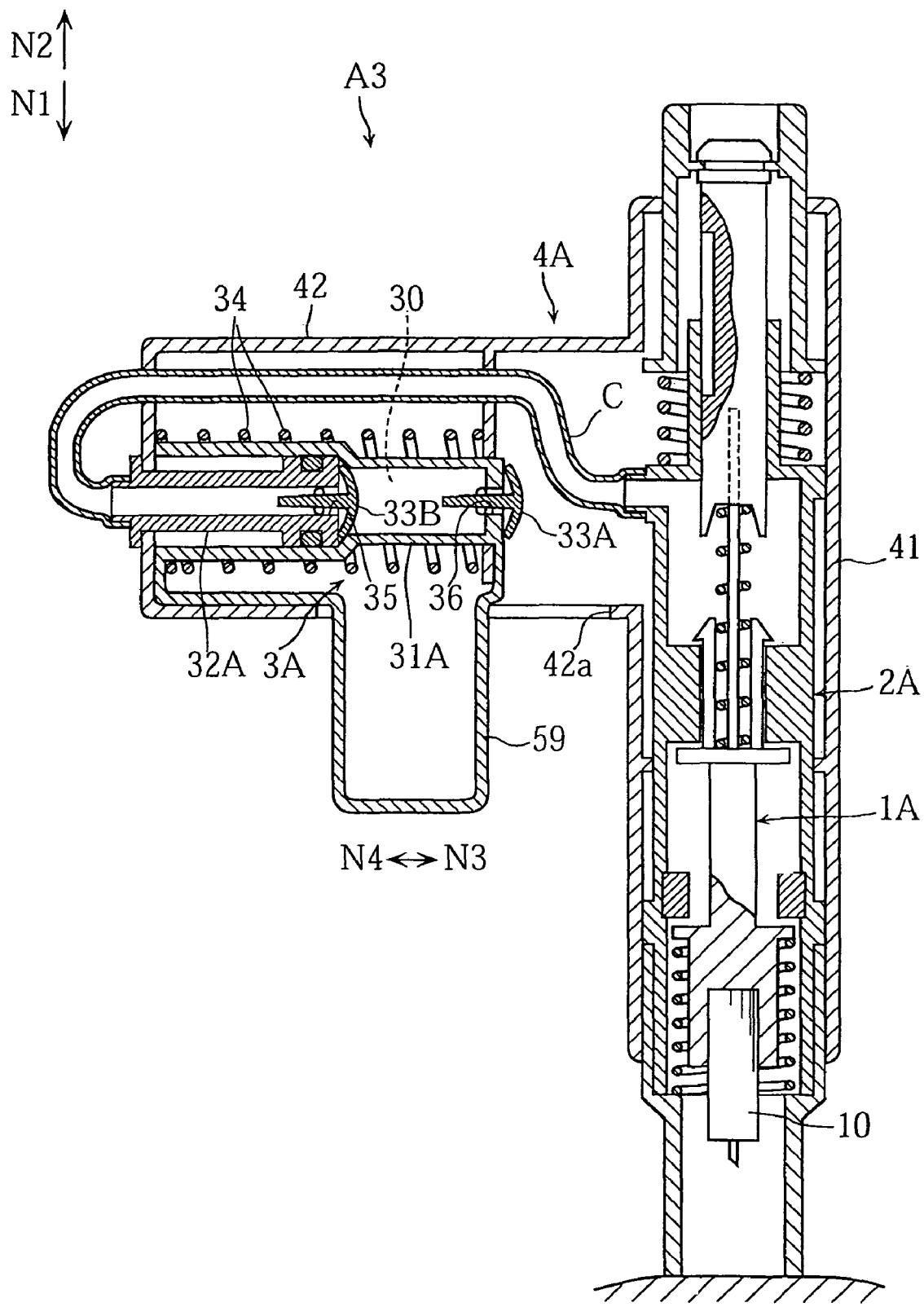
FIG. 13 is a sectional view of a lancing device according to a third embodiment of the present invention.

As shown in FIG. 13, the lancing device A3 has a pump mechanism 3A perpendicular to the direction N1 or the direction in which the lancet 10 moves. Accordingly, an operative casing 4A includes a first portion 41 incorporating a lancet holder 1A and others, and a second portion 42 extending perpendicularly (in a direction N4) from the first portion 41 and incorporating the pump mechanism 3A.

The pump mechanism 3A uses basically the same arrangement as in the lancing device A1. Specifically, the pump mechanism 3A includes a plunger 32A having an air intake port 35, a cylinder 31A having an air discharge port 36 and forming a pressure chamber 30 together with the plunger 32a, check valves 33A, 33B, and a return spring 34.

A difference however, is that the cylinder 31A is fixed to an operative portion 59. The operative portion 59 projects out of an opening 42a formed in a second portion 42 of an operative casing 4A. On the other hand, the plunger 32A is fixed to the second-portion 42 of the operative casing 4A. The plunger 32A is connected to a housing 2A via a tube C. Thus, the inside of the pressure chamber 30 communicates with the inside of the housing 2A via a through hole of the plunger 32A and via the tube C.

In the pump mechanism 3A, when a force is applied on the operative portion 59 in a direction indicated by an arrow N3, the cylinder 31A moves in the direction N3 to increase the capacity of the pressure chamber 30. In this movement, the check valve 33B opens to allow the air in the housing 2A to flow through the tube C and into the pressure chamber 30, causing a vacuum in the housing 2A. At the same time, an elastic force is stored in the return spring 34. On the other hand, when the force applied in the direction N3 is removed, the elastic force from the return spring 34 moves the cylinder 31A in the direction N4. In this movement, the check valve 33A opens to discharge the air from the pressure chamber 30 through the air discharge port 36, reducing the capacity of the pressure chamber 30.

Next, a lancing device A4 according to a fourth embodiment of the present invention will be described with reference to FIG. 14A and FIG. 14B. In these figures, members and elements identical with or similar to those in the lancing devices A1 through A3 described already are given the same alphanumeric codes and their description will not be repeated here.

Figure 14A:
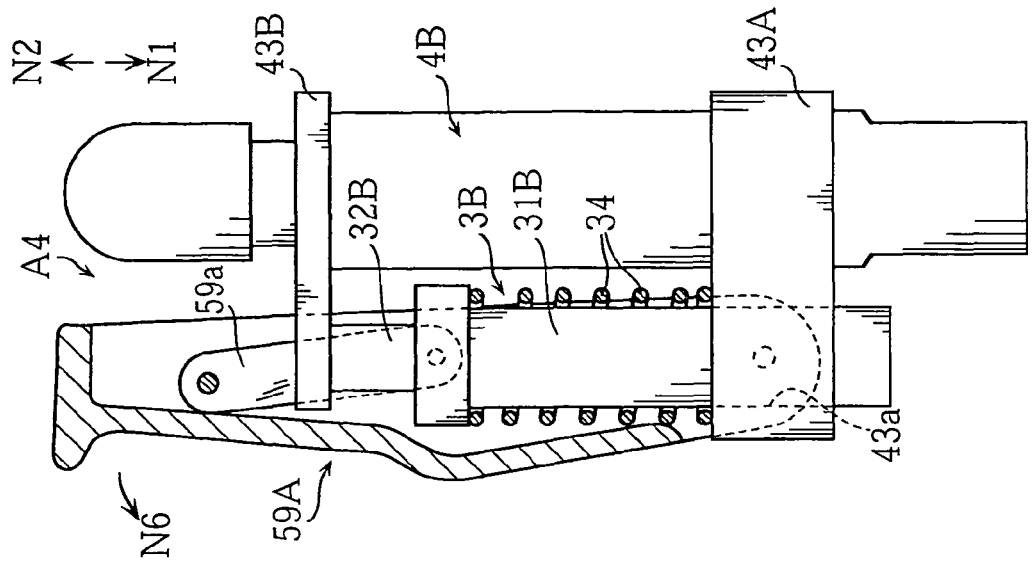
FIG. 14A and FIG. 14B are sectional views of a lancing device according to a fourth embodiment of the present invention.
Figure 14B:
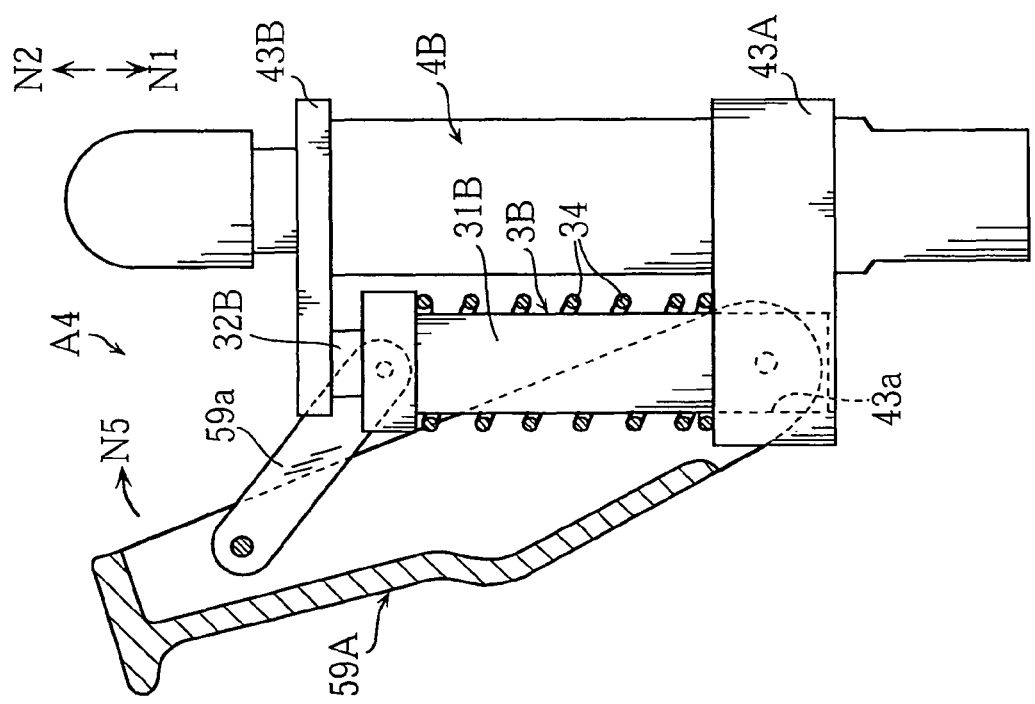

In the lancing device A4, as shown in FIG. 14A and FIG. 14B, a vacuum can be created by reciprocation of an operative lever 59A in directions indicated by arrows N5, N6. Again in this embodiment, the lancing device A4 includes a pump mechanism 3B which is similar to those used in the lancing devices A1 through A4. However, the actual arrangement used for the pump mechanism is basically the same as in the lancing device A1. Specifically, the pump mechanism 3B includes a cylinder 31B, a plunger 32B, a return spring 34, and check valves (not illustrated).

An operative casing 4B includes two supports 43A, 43B. The support 43A pivotably supports the operative lever 59A. The support 43A has a through hole 43a. The through hole 43a allows the cylinder 31B to move in the directions N1, N2, and guides the movement of the cylinder 31B. The cylinder 31B has an upper end serving as a stopper. Between this stopper and the support 43A, a spring 34 is provided around the cylinder 31B. On the other hand, the support 43B holds the plunder 32B. The cylinder 31B has an upper end linked to the operative lever 59A by a link member 59a. Though not illustrated, the inside of the housing (not illustrated) communicates with the inside of the plunger 32B via a passage provided in the support 43B.

In the lancing device A4, the operative lever 59A is moved in the direction N5 to move the cylinder 31B in the direction N1 thereby to increase the capacity of the pressure chamber. This allows the air in the housing to flow into the pressure chamber, creating a vacuum in the housing. In this step, the return spring 34 stores an elastic force. On the other hand, when the force acting on the operative lever 59A is removed, the elastic force from the return spring 34 moves the cylinder 31B in the direction N2, causing the link member 59a to move the operative lever 59A in the direction N6. In this step, the air is discharged from the pressure chamber, and the capacity of the pressure chamber decreases.

Next, a lancing device A5 according to a fifth embodiment of the present invention will be described with reference to FIG. 15 through FIG. 22. In these figures, members and elements identical with or similar to those in the lancing devices A1 through A4 described already are given the same alphanumeric codes and their description will not be repeated here.

The lancing device A5 according to the present embodiment includes a housing 2C, which incorporates a pump mechanism 3C driven by an operative casing 4C, and a lancing mechanism actuated by an operative cap 5C. The housing 2C is provided by three sleeves 20CA through 20CC connected together.

Figure 16:
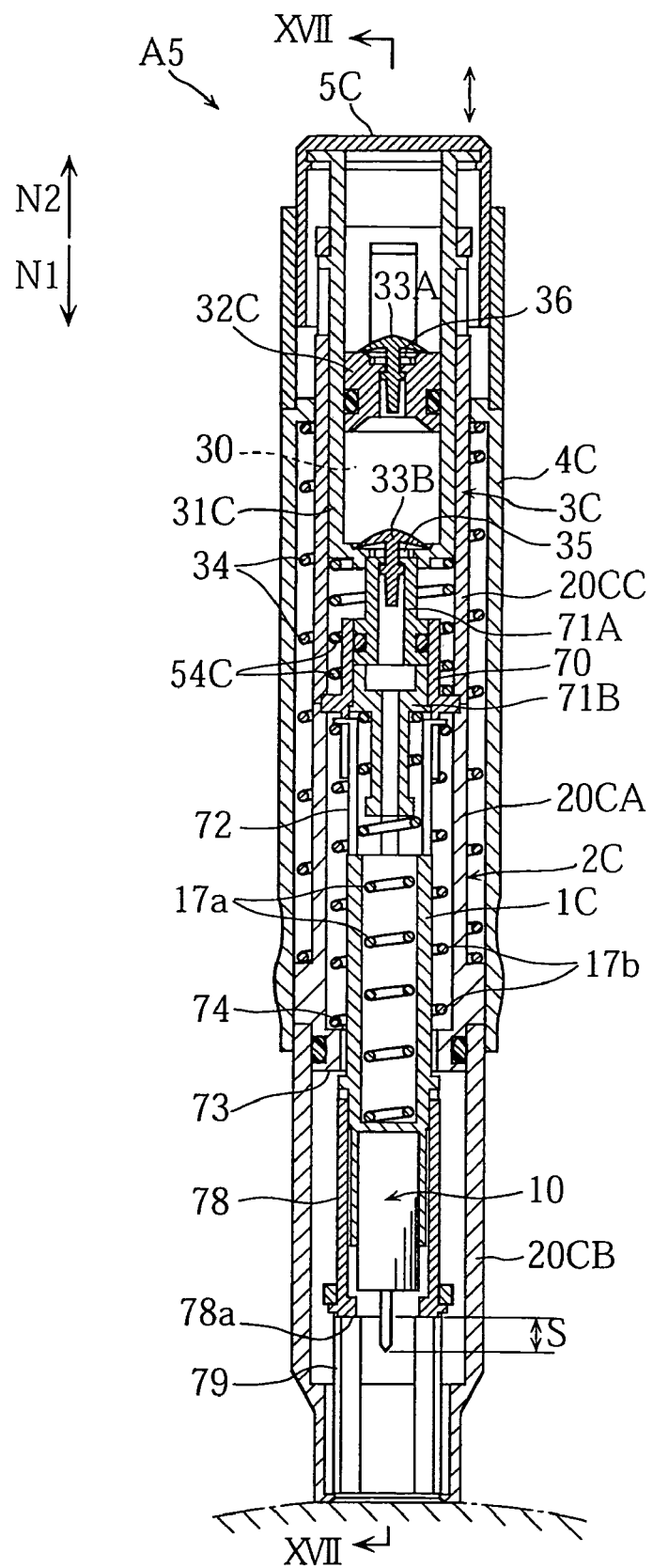
FIG. 16 is a sectional view taken in lines XVI-XVI in FIG. 15.

As shown in FIG. 16, the pump mechanism 3C includes a pressure chamber provided by a cylinder 31C and a plunger 32C, and a first and a second check valves 33A, 33B.

The operative casing 4C is fitted around the housing 2C and can reciprocate axially in directions N1, N2 relatively to the housing 2C. When the operative casing 4C is pressed down relatively to the housing 2C, a spring 34 moves the operative casing 4C back into the original position.

The cylinder 31C is fitted into an upper portion (a head) of the housing 2C and can reciprocate within a predetermined stroke range. Above the cylinder 31C, an operative cap 5 projects out of the upper end of an outer cylinder 2, to allow a pressing operation. When the operative cap 5C is pressed down, the cylinder 31C also comes down. A spring 54C is provided below the cylinder 31C. The coil spring 54 moves the cylinder 31C back to the original position after it is lowered.

The plunger 32C is fitted in and can reciprocate with respect to the cylinder 31C. As clearly shown in FIG. 17, the plunger 32C includes a pair of arms 37 for connection with an upper portion of the operative casing 4C. Therefore, when the operative casing 4C is reciprocated in directions N1, N2, the cylinder 31C also reciprocates in the cylinder 31C.

The check valve 33A opens and closes an air discharge port 36 and is attached to the plunger 32C. The check valve 33A allows the air to flow from the pressure chamber 30 to the outside, but blocks the air flowing from the outside into the pressure chamber 30.

The cylinder 31C has a bottom provided with an air intake port 35 for allowing the air inside the housing 2C to flow into the pressure chamber 30. The housing 2C includes a series of passages connecting the air intake port 35 to the inside of the front end of the housing 2C. More specifically, the air intake port 35 communicates with the inside of the front end of the housing 2C via through holes formed in a first and a second pushers 71A, 71B to be described later, a plurality of slits 72 provided at an upper portion of a lancet holder 1C, and a gap 74 between a step 73 of the housing 2C and the lancet holder 1C.

The check valve 33B opens and closes the air intake port 35. The check valve 33B allows the air to flow from the outside of the pressure chamber 30 into the pressure chamber 30, but blocks the air flowing from the pressure chamber 30 to the outside.

Figure 18:
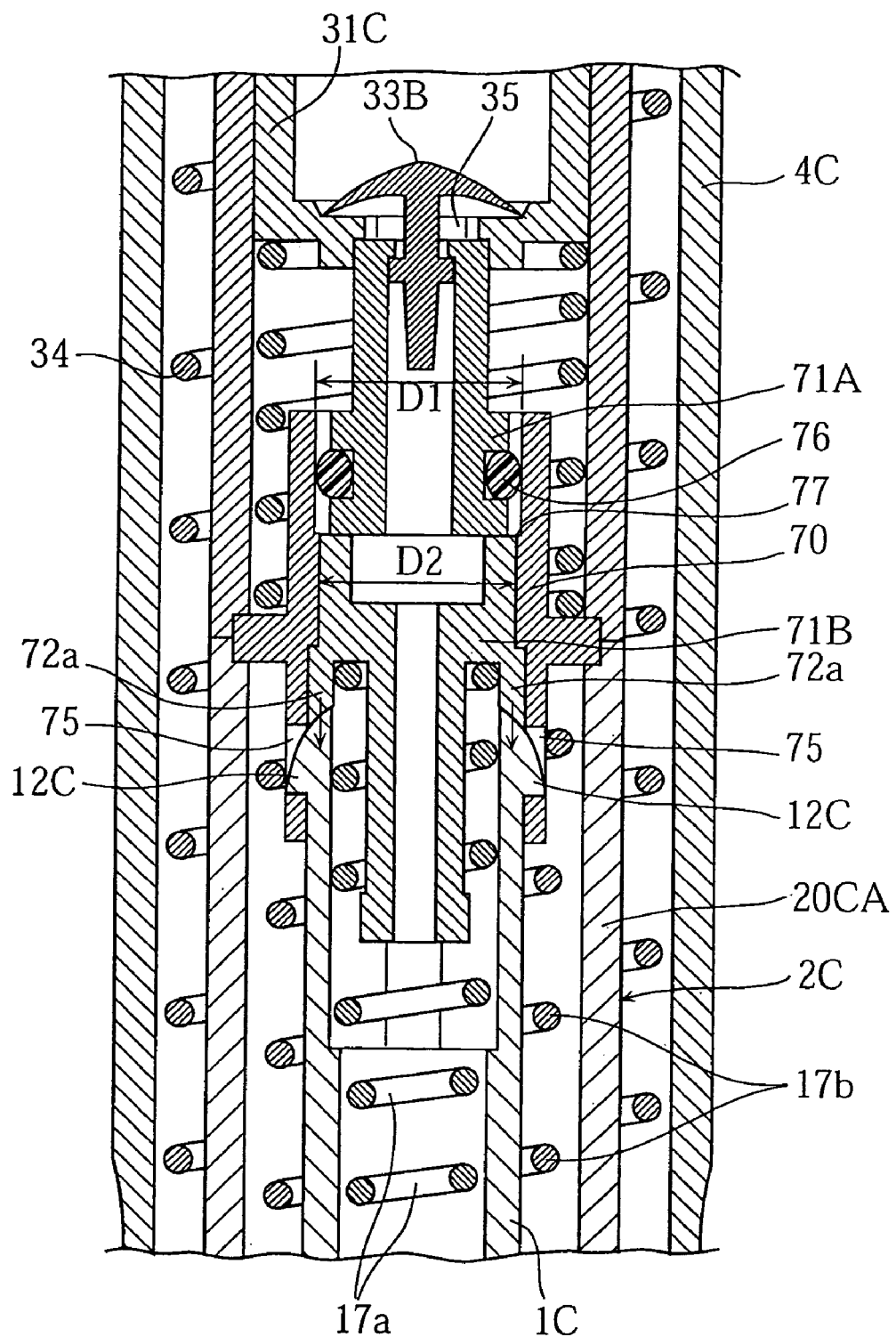
FIG. 18 is an enlarged view of a primary portion in FIG. 17.
Figure 19:
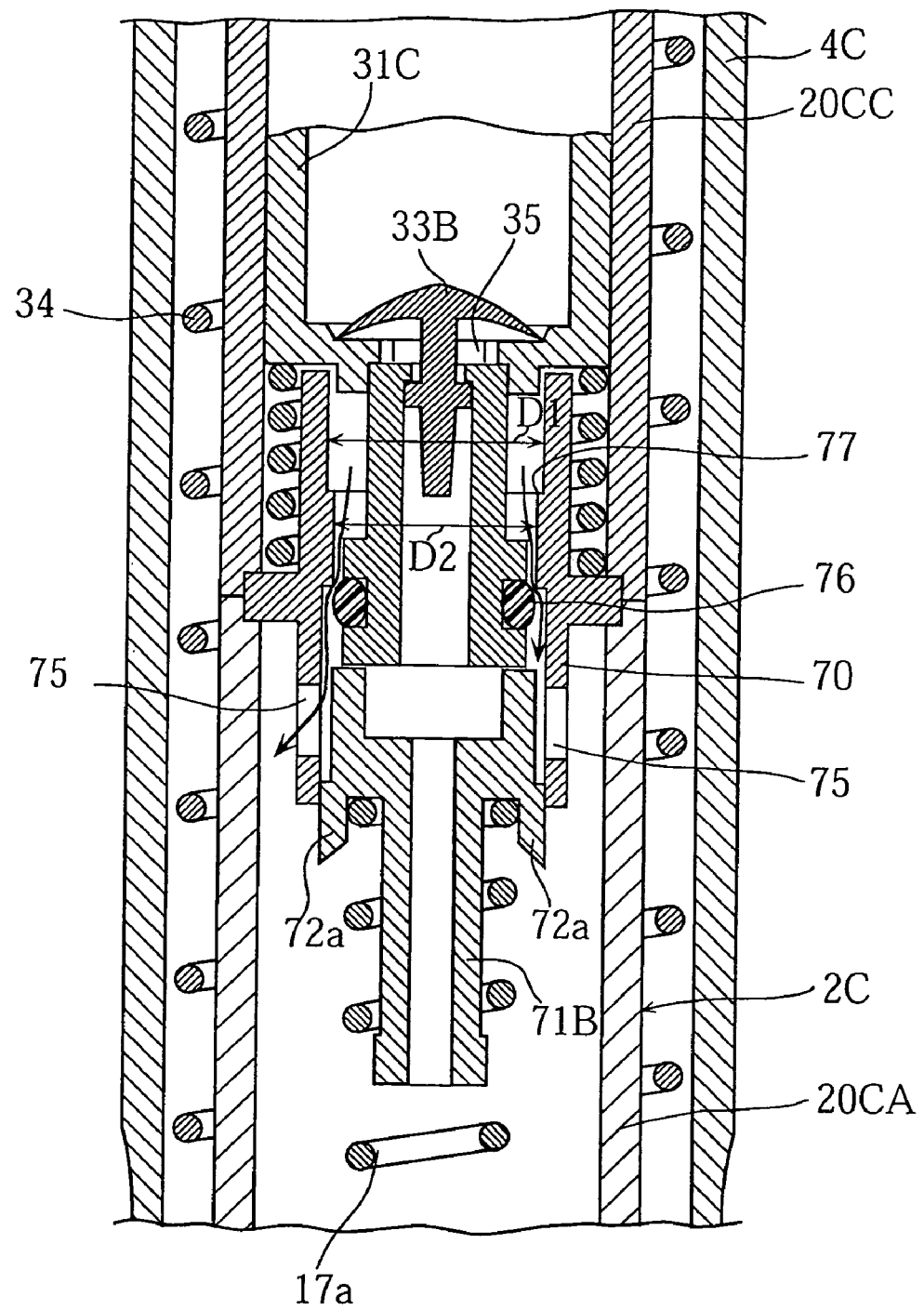
FIG. 19 is a diagram for describing actions in the portion shown in FIG. 18.
Figure 21:
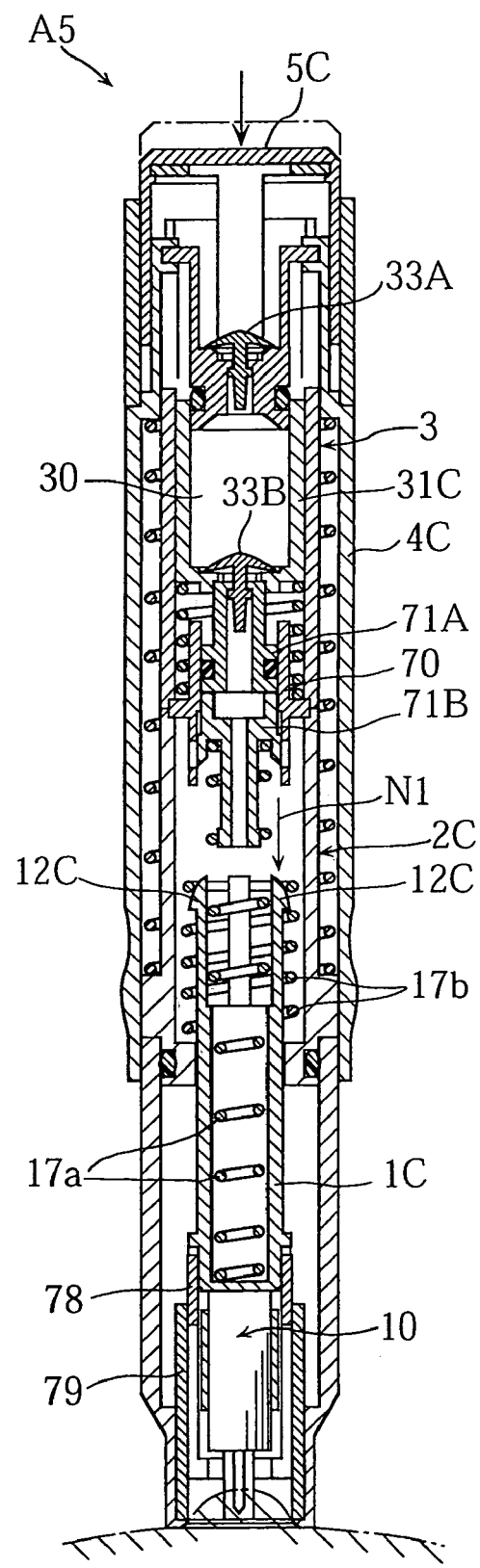
FIG. 21 is a sectional view for describing a lancing operation in the lancing device in FIG. 15 through FIG. 17.

As clearly shown in FIG. 18, the lancing mechanism moves the lancet holder 1C toward the front end. The lancing mechanism includes a sleeve 70, and the first and the second pushers 71A, 71B which can reciprocate therein. The sleeve 70 is fixed in the housing 2C and below the cylinder 31C. Close to a lower end of the sleeve 70, a pair of holes 75 is formed for a pair of latching pawls 12C to engage. The lancet holder 1C has an upper portion incorporating a coil spring 17a having an upper end contacting the second pusher 71B. The lancet holder 1C can be latched to the sleeve 70 by the engagement between the latching pawls 12C and the holes 75 while the coil spring 17a is compressed.

The first pusher 71A, connected to the bottom of the cylinder 31C, can reciprocate with the cylinder 31C. The first pusher 71A has a lower end fitted into the sleeve 70. The second pusher 71B, which has an upper end fitted into the sleeve 70, can reciprocate in the sleeve, and is contacted to the bottom of the first pusher 71A by an elastic force from the coil spring 17a. The second pusher 71B is an example of the unlatching portion according to the present invention, and has a pair of projections 72a located above the respective engaging pawls 12C of the lancet holder 1C. Each of the projections 72a and the engaging pawls 12C is formed with a predetermined tapered surface to fit each other. When the projections 72a come down below their position shown in FIG. 18, the projections 72a presses the respective engaging pawls 12C to deform inwardly, releasing the engagement between the engaging pawls 12C and the sleeve 70. The lancet holder 1C is surrounded by a coil spring 17b. The coil spring 17b moves the lancet holder 1C in the direction N2 after a puncture is made.

The first pusher 71A is fitted with an O ring 76 made of rubber for example, to keep air tightness between the first pusher 71A and the inner wall of the sleeve 70. However, the inner wall of the sleeve 70 has a step 77, so that the amount of resistance changes as the operative cap 5C is pressed to move the first pusher 71A down. More specifically, an inner diameter D1 of an upper portion of the sleeve 70 is slightly larger than the inner diameter D2 of the lower portion. During the downward movement of the O ring 76 moving with the first pusher 71A, when the second pusher 71B unlatches the engagement between the engaging pawls 12C and the sleeve 70, the O ring 76 come right at the step 77. As clearly shown in FIG. 19, the first pusher 71A can come as far as the O ring 76 has passed the portion having the diameter D2, upon which the air tightness between the first pusher 71A and the sleeve 70 is lost.

The lancet holder C1 has a tip provided with an assisting cap 78 surrounding a lancet 10. When the lancet holder 1C moves forward, a front face 78a of the assisting cap 78 makes contact with the skin, allowing only a portion of the lancet 10 projecting out of the front face 78 to stick into the skin. With this arrangement, the assisting cap 78 can be made movable axially of the lancet holder 1C so that the amount of projection S of the lancet 10 out of the assisting cap 78 can be adjusted. Then, the depth to which the lancet 10 is driven can be varied freely. According to the present invention, however, it is not essential to include such means. Inside the front end of the housing 2C, a generally tubular guide 79 is provided for guiding the forward movement of the assisting cap 78. The guide 79 and a front end portion of the housing 2C can be transparent so that bleeding from the skin can be visually observed.

Next, a use example and function of the lancing device A5 having the above arrangement will be described.

Figure 15:
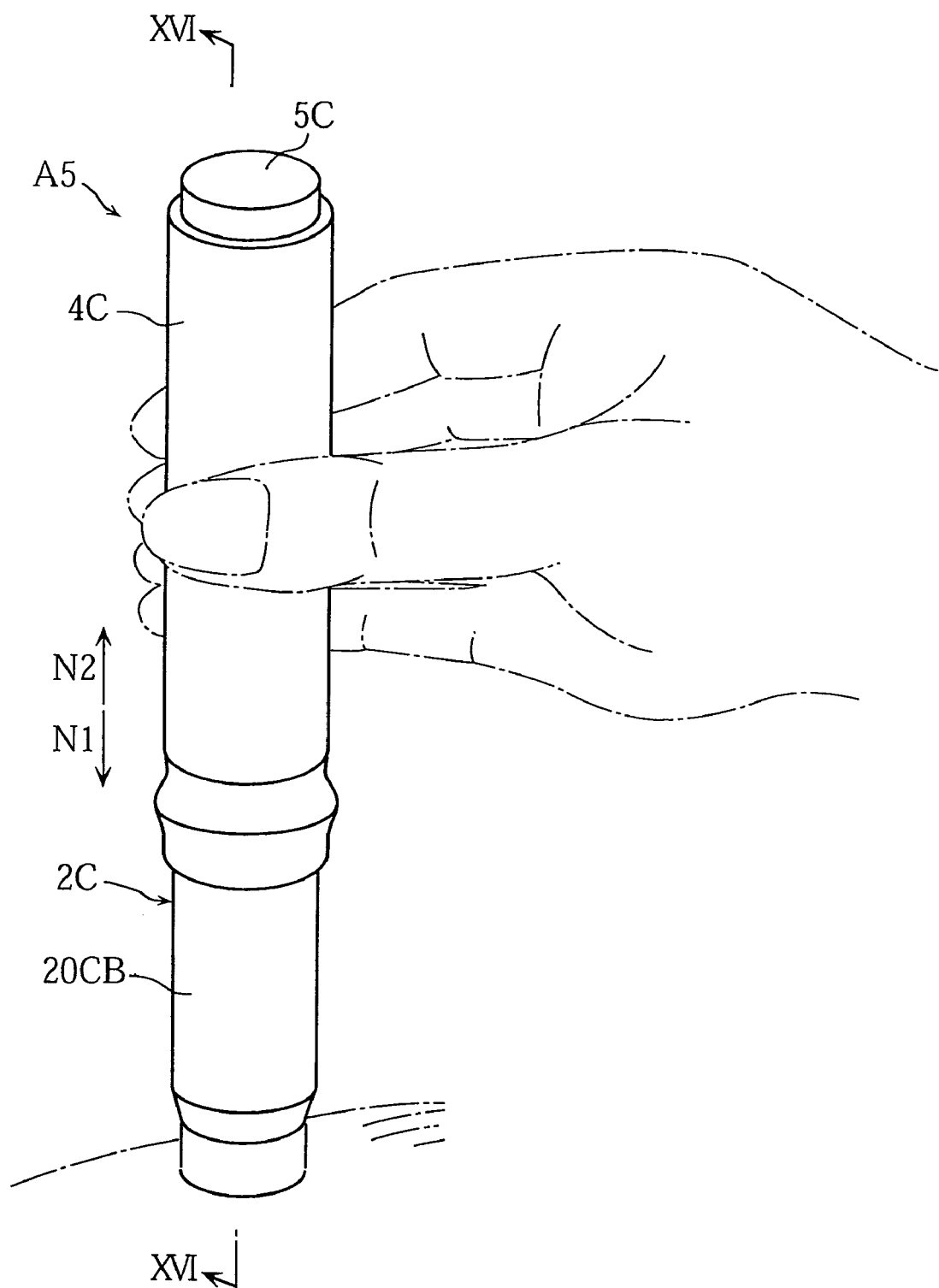
FIG. 15 is an overall perspective view of a lancing device according to a fifth embodiment of the present invention.
Figure 17:
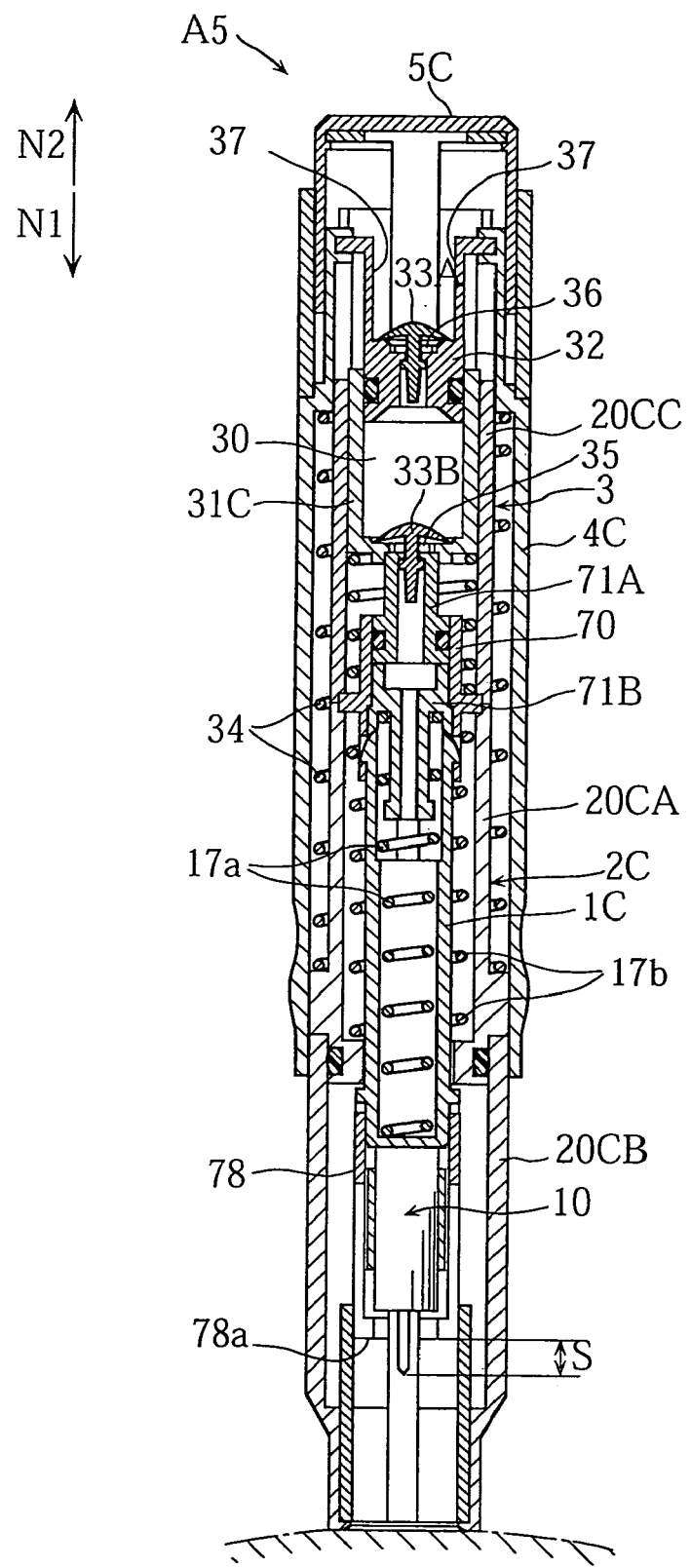
FIG. 17 is a sectional view taken in lines XVII-XVII in FIG. 16.

As shown in FIG. 16 and FIG. 17, when the lancing device A5 is used, the lancet holder 1C fitted with the lancet 10 is latched to the sleeve 70. Next, as shown in FIG. 15, the front end of the housing 2C is held onto the skin. If a vacuum is desired, the operative casing 4C is moved up and down. The operative casing 4C is easy to grip, and has a good operability because the coil spring 34 raises the operative casing 4C after the operative casing 4C has been pressed down.

As shown in FIG. 20, when the operative casing 4C moves down in the direction N1, the plunger 32C comes down also. In this step, the check valve 33B is closed whereas the check valve 33A is open, allowing smooth discharge of the air from the pressure chamber 30 to the out side of the housing 2C via the air discharge port 36. On the contrary, as shown in FIG. 20B, when the operative casing 4C moves up in the direction N2, the plunger 32C also comes up, increasing the capacity of the pressure chamber 30 thereby creating a vacuum in the pressure chamber 30. In this step, the check valve 33A is closed whereas the check valve 33B is open. Therefore, a vacuum also is created inside the front end of the housing 2C and acted on the skin.

Following the above operation, if the operative casing 4C is continued to be reciprocated, the check valve 33B, which closes when the plunger 32C moves down, properly maintains the vacuum in the inside of the front end of the housing 2C. Thus, it is possible to gradually increase the negative pressure (decrease the absolute air pressure value) inside the pressure chamber 30 and the front end of the housing 2C for each reciprocation of the operative casing 4C. As a result, according to the lancing device A5, it is possible to appropriately adjust the level of vacuum acting on the skin, by increasing or decreasing the number of reciprocating operations.

Next, in order to drive the lancet L, the operative cap 5C is pressed down using a finger. In this operation, the cylinder 31C and the first and the second pushers 71A, 71B move down relatively to the housing 2C, causing the second pusher 71B to press each of the engaging pawls 12C of the lancet holder 1C, thereby unlatching the lancet holder 1C from the sleeve 70. Then, as clearly shown in FIG. 21, the lancet holder 1C is shot toward the front end opening of the housing 2C, in the direction N1 by an elastic force from the coil spring 17a, causing the lancet 10 to stick into the skin. From this state, if the user is about to press the operative cap 5C further, the O ring 76 of the first pusher 71A shown in FIG. 18 moves in the sleeve 70, from a place having the diameter D1 to a place having the diameter D2, to generate a greater resistance. Thus, based on such an increase in the resistance, the user can properly percept the completion of the forward movement of the lancet 10. Once the lancet 10 is driven into the skin, the coil spring 17b moves back the lancet holder 1C by an appropriate amount, thereby pulling the lancet 10 out of the skin.

Figure 22:
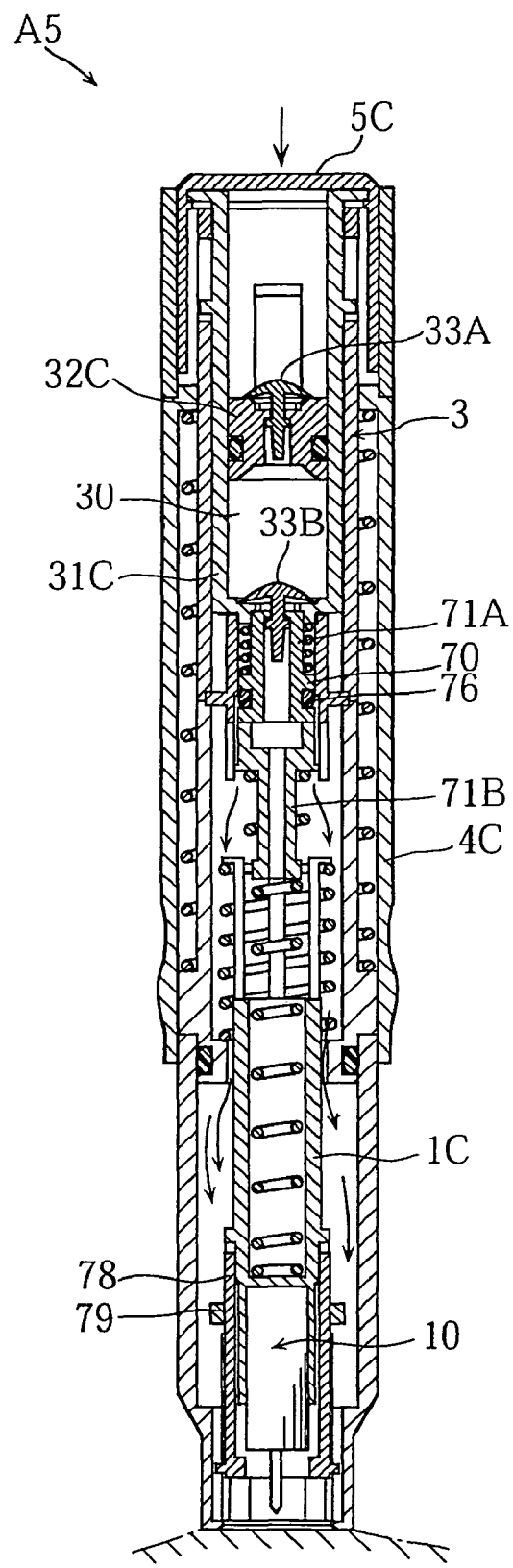
FIG. 22 is a sectional view for describing a vacuum canceling operation in the lancing device in FIG. 15 through FIG. 17.

As shown in FIG. 22, when the operative cap 5C is further pressed thereafter, then as shown in FIG. 18, the O ring 76 comes down in the sleeve 70, to pass the place having the inner diameter D2. This breaks the air tightness in the passage, from inside the front end of the housing 2C to the air discharge port 36 of the cylinder 31C, and the atmospheric pressure comes inside the front end of the housing 2C, allowing the housing 2C to be removed easily from the skin.

According to the lancing device A5, a vacuum acting on the skin cannot be released unless the operative cap 5C is pressed further after the operative cap 5C is first operated to drive the lancet 10 into the skin. This arrangement makes sure that the vacuum acting on the skin is not mistakenly lost before the lancet 10 is driven. Therefore, a proper sequence of operations is assured; the skin is properly bulged and stimulated by partial vacuum for improved blood flow before the lancet 10 is driven. Further, both driving of the lancet 10 and releasing of the partial vacuum can be made continuously by pressing the operative cap 5C, resulting in simplified operation for these steps.

According to the use example described above, a vacuum is first created in the housing 2C, and then the lancet 10 is driven into the skin. Alternatively, according to the lancing device A5, the steps may be reversed. Namely, the sequence may be that the operative cap 5C is pressed to drive the lancet 10 into the skin first, and then the operative casing 4C is operated to create partial vacuum on the place pricked by the lancet 10. This sequence too can promote bleeding from the place pricked by the lancet 10, by means of vacuum. As described, the lancing device A5 is convenient in that the user can select whether the partial vacuum should be created before or after the lancet 10 is driven into the skin. Further, according to the lancing device A5, when the operative casing 4C is reciprocated in order to create a vacuum, the tip of the housing 2C gives a massage to the skin, potentially resulting in further improvement in the blood flow in the skin.

According to the lancing device A5, the cylinder 31C for creating a vacuum is placed inside the housing 2C. With this arrangement, when the operative cap 5C is pressed, the cylinder 31C helps the unlatching action to release the lancet holder 1C. Further, since the air discharge port 36 and the check valve 33A are provided in the plunger 32C, these components do not project out of the cylinder 31C. Further, the passages from inside the front end of the housing 2C to the air intake port 35 are provided by through holes formed through the center of the first and the second pushers 71A, 71B. Thus, according to the lancing device A5, space-efficient, rational assembly of components is achieved, making possible to slim down the overall size.

The return spring 34 of the plunger 32C is provided in a space-efficient manner between the operative casing 4C and the housing 2C, and there is no return springs or other components placed in the pressure chamber 30. Therefore, according to the lancing device A5, as compared to a case in which the pressure chamber 30 incorporates a return spring or the like, the effective volumetric capacity of the pressure chamber 30 can be increased, making it possible to create a high level of vacuum with a single reciprocating stroke of the plunger 32C. This helps decrease the number of reciprocating strokes of the operative casing 4C and the plunger 32C necessary for creating a given level of vacuum.

Figure 23:
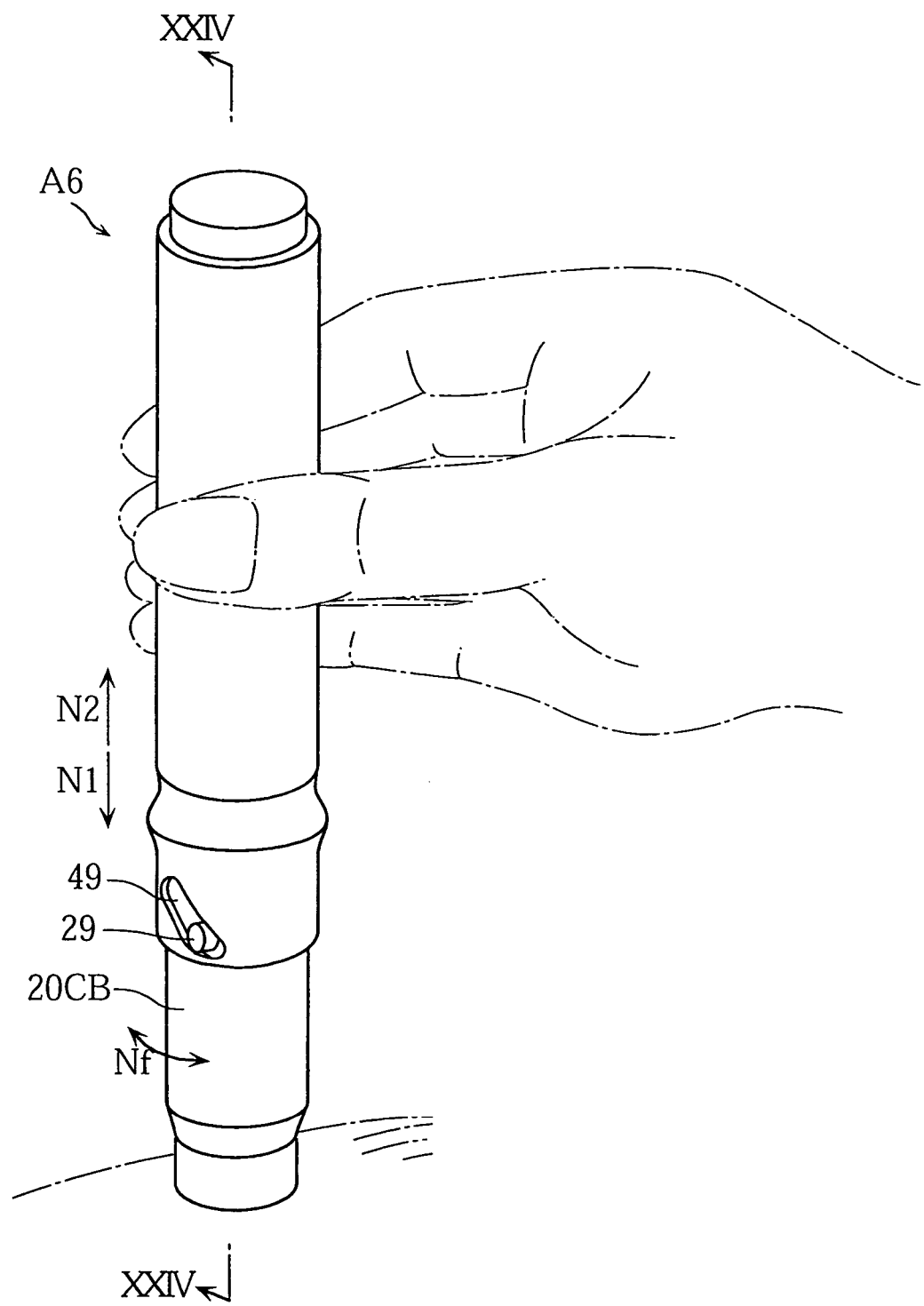
FIG. 23 is an overall perspective view of a lancing device according to a sixth embodiment of the present invention.
Figure 24:
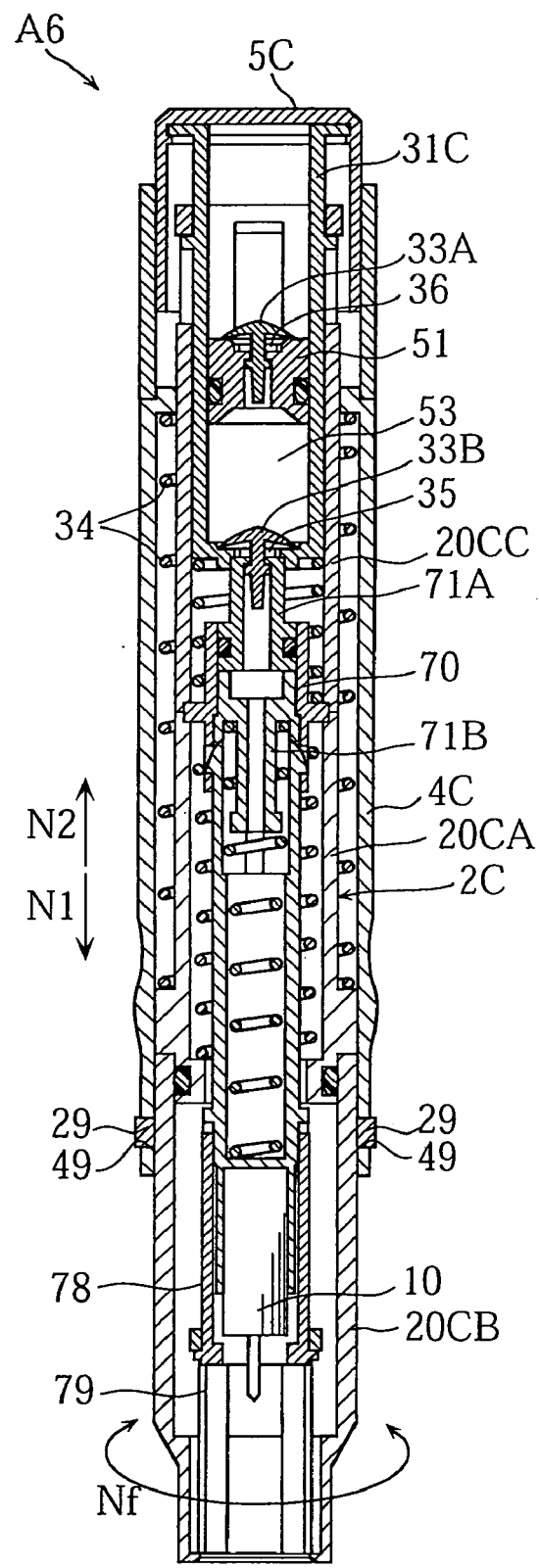
FIG. 24 is a sectional view taken in lines XXIV-XXIV in FIG. 23.

FIG. 23 and FIG. 24 show a lancing device according to a sixth embodiment of the present invention. In these figures, members and elements identical with or similar to those in the lancing devices A1 through A5 described already are given the same alphanumeric codes and their description will not be repeated here.

The A6 includes an operative casing 4C having a front end outer wall formed with a pair of helical long holes 49. A housing 2C includes a second tube 20B having a front end outer wall formed with projections 29 to correspond to the long holes 49 respectively. When the operative casing 4C is moved up and down in the directions N1, N2, the projections 29 guided in the long holes 49 make a sleeve 20CB rotate in a direction indicated by an arrow Nf.

According to such an arrangement, when the operative casing 4C is moved up and down for creating a vacuum inside the front end of the housing 2C, the sleeve 20CB contacting the skin makes rotating action simultaneously, giving a massage to the skin. Therefore, bleeding is promoted not only by the partial vacuum in the housing 2C but also by the massaging action, making it easy to take blood samples from places where it is difficult to cause bleeding.

Figure 25:
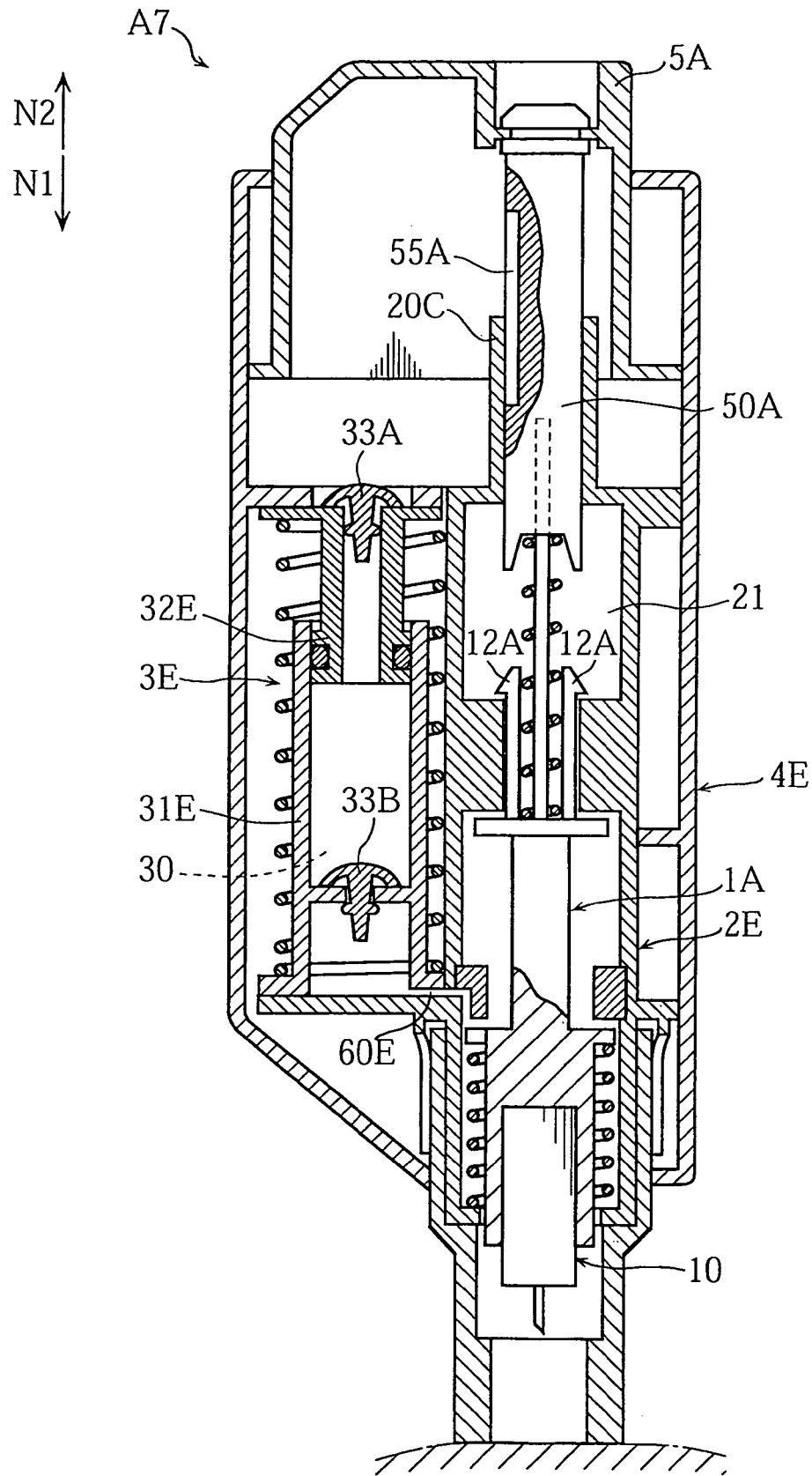
FIG. 25 is a sectional view of a lancing device according to a seventh embodiment of the present invention.
Figure 26:
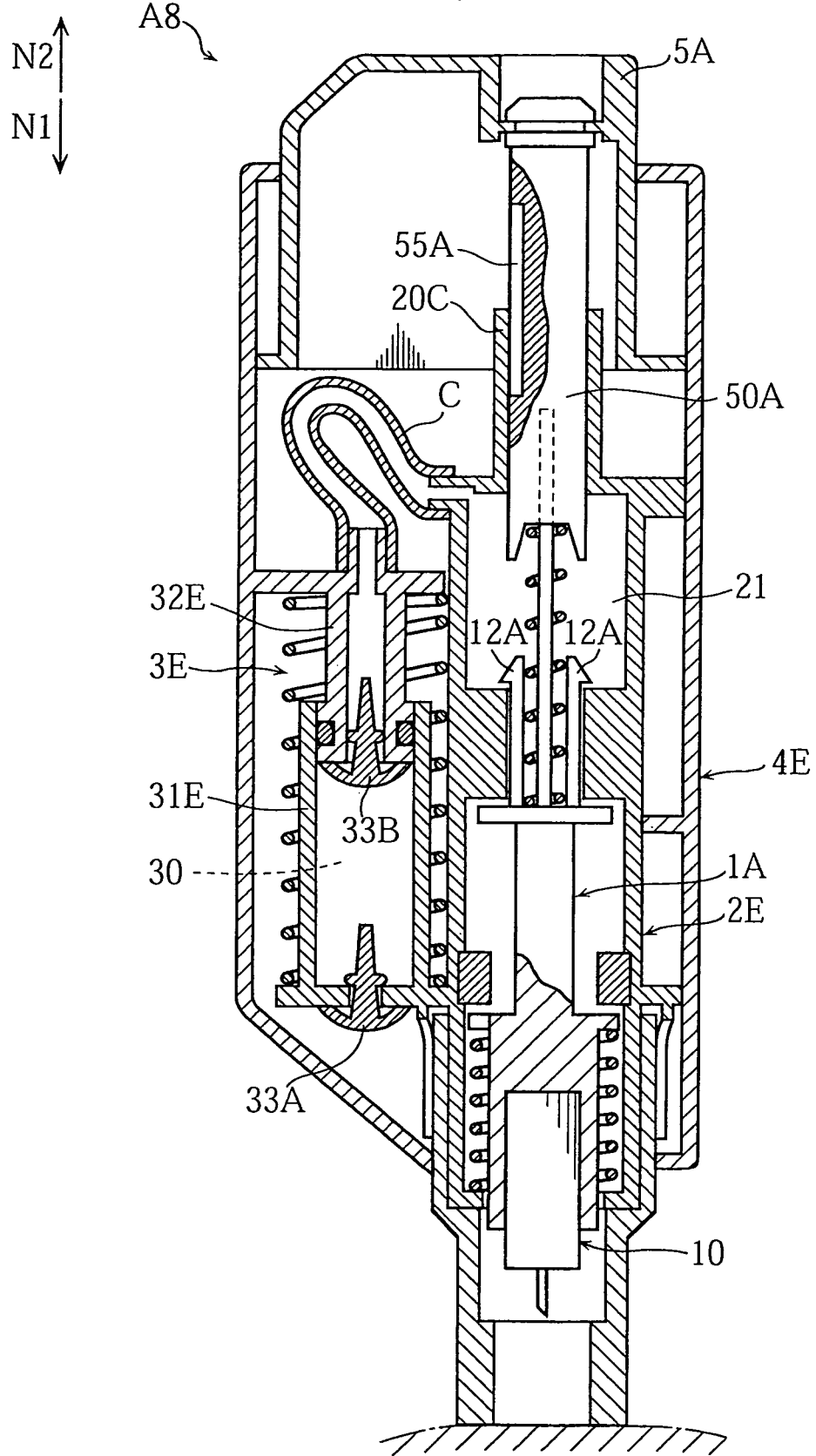
FIG. 26 is a sectional view of a lancing device according to an eighth embodiment of the present invention.
Figure 27:
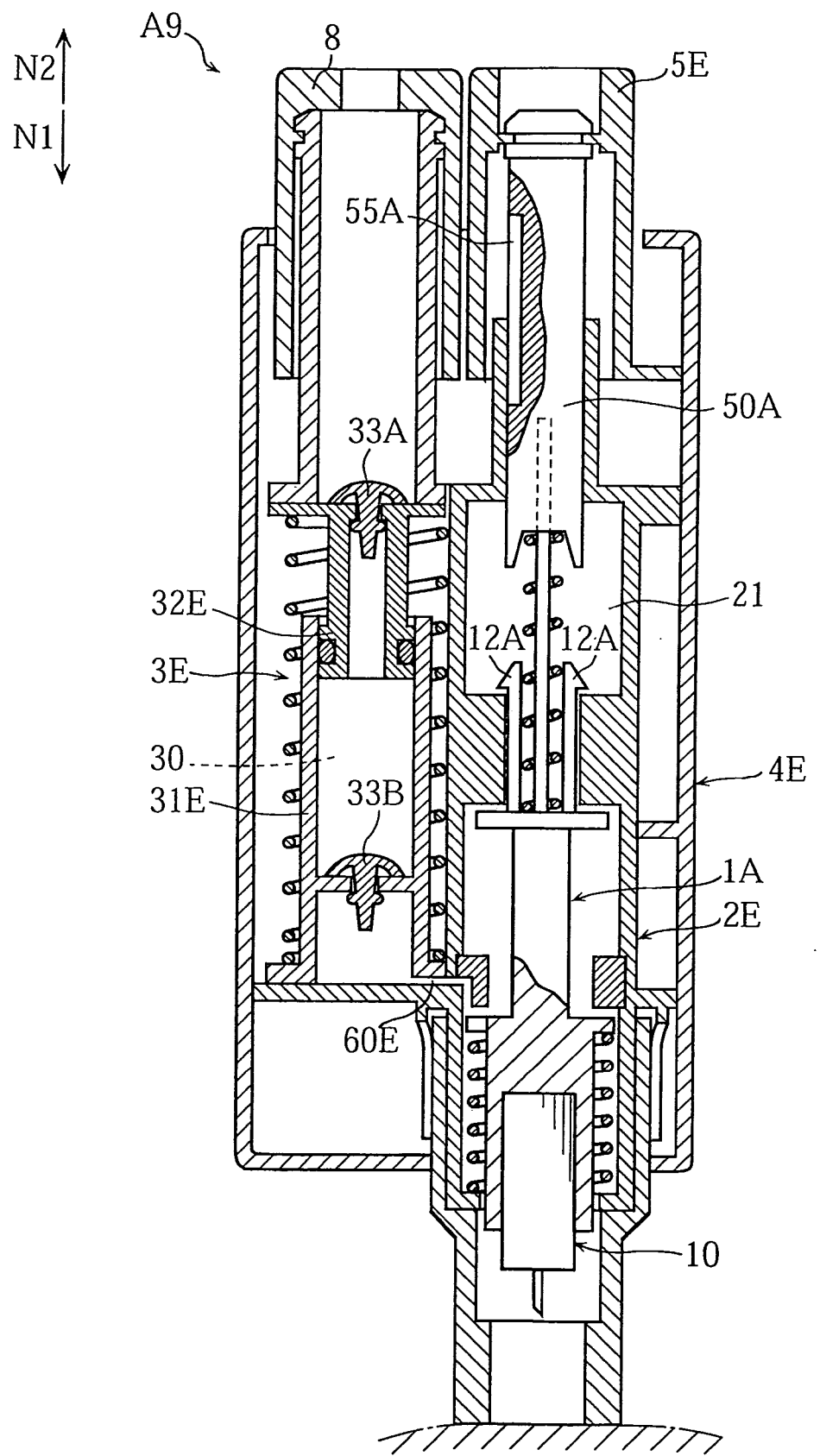
FIG. 27 is a sectional view of a lancing device according to a ninth embodiment of the present invention.

FIG. 25 through FIG. 27 show lancing devices according to a seventh to a ninth embodiments of the present invention. In the lancing devices A7 through A9 shown in these figures, a pump mechanism 3E and a housing 2E are placed side by side.

In the lancing device A7 shown in FIG. 25, communication with the housing 2E is achieved via a passage 60E provided in the cylinder 31E. On the other hand, in the lancing device A8 shown in FIG. 26, a plunger 32E communicates with the housing 2E via a tube C. In these lancing devices A7, A8, vertical reciprocation of an operative casing 4E causes the plunger 32E to move and thereby varies the capacity of the pressure chamber 30. With this arrangement, the level of vacuum in the housing 2E can be adjusted by the number of reciprocations of the operative casing 4E.

The A9 shown in FIG. 27 includes an operative button 8 which serves a different purpose from an operative cap 5E which is for making a puncture. When the operative button 8 is pressed in the direction N1, the plunger 32E moves downward to decrease the capacity of the pressure chamber 30.

According to the lancing device A9, the level of vacuum in the housing 2E can be adjusted by the number of reciprocations made to the operative button 8.

The lancing device according to the present invention is not limited to those embodiments described here above, and specifics of the members and components can be varied in many ways.

For example, the first and the second check valves may be of a type different from the one used in the embodiments. Further, a plurality of these valves may be used, and there is no limitation to the number of the valves.

Figure 28:
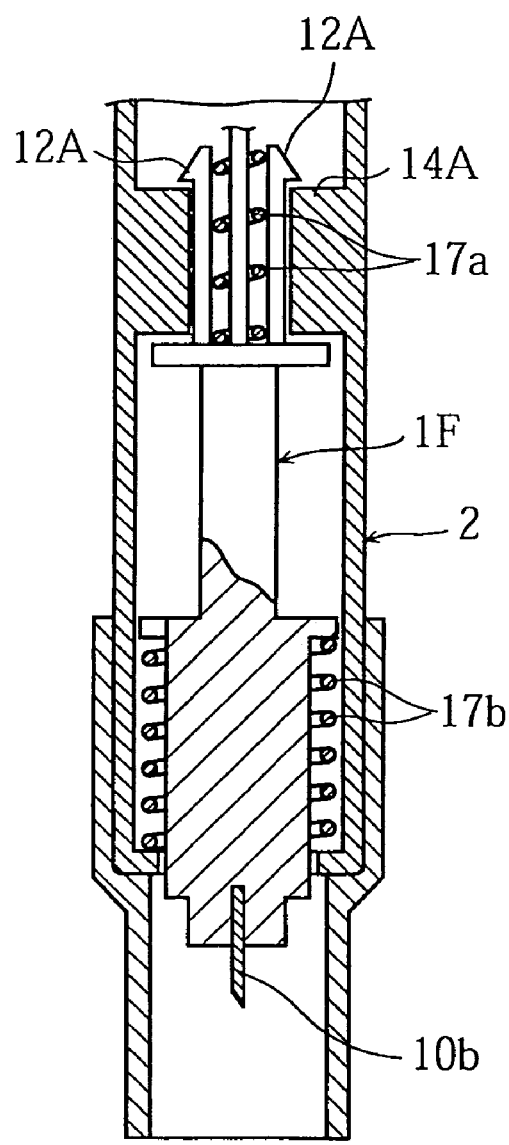
FIG. 28 is a sectional view of a primary portion, showing another application of the present invention.

The present invention is applicable not only to the type of lancing device including a lancet holder that holds a lancet, but also to other types, such as shown in FIG. 28, in which a moving body 1F, which corresponds to the lancet holder, integrally includes a needle 10b.

Figure 29:
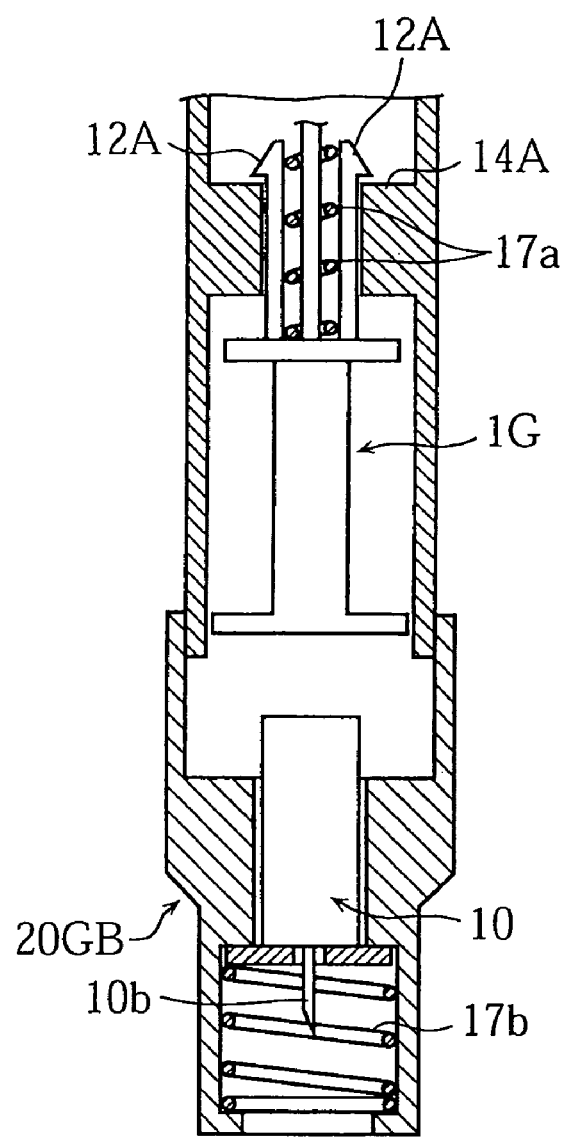
FIG. 29 is a sectional view of a primary portion, showing another application of the present invention.

Further, the present invention is also applicable to a type shown in FIG. 29, in which a lancet 10 is held in a cover (sleeve) 20GB, and the lancet 10 (needle 10b) is moved by a thrust from a hammer 1G. The movement of the hammer 1G is actuated by the latch mechanism described earlier. According to this arrangement, when the hammer 1G is unlatched, the hammer 1G moves toward the front end, shooting the lancet 10 toward the front end to drive the needle 10b into the skin. Upon making the puncture, an elastic force from the coil spring 17b moves the lancet 10 in the reverse direction, pulling the needle 10b out of the skin.

Figure 30:
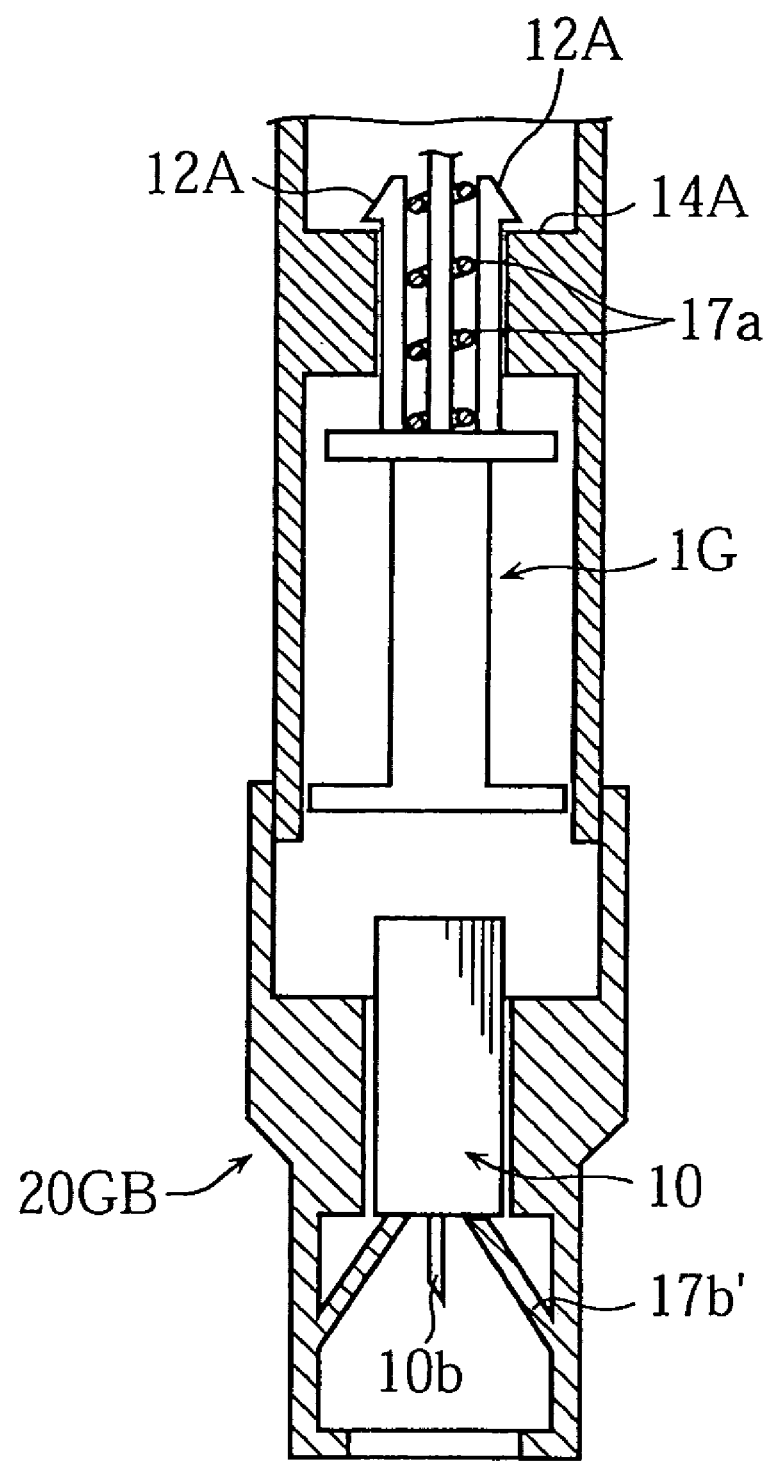
FIG. 30 is a sectional view of a primary portion, showing another application of the present invention.
Figure 31:
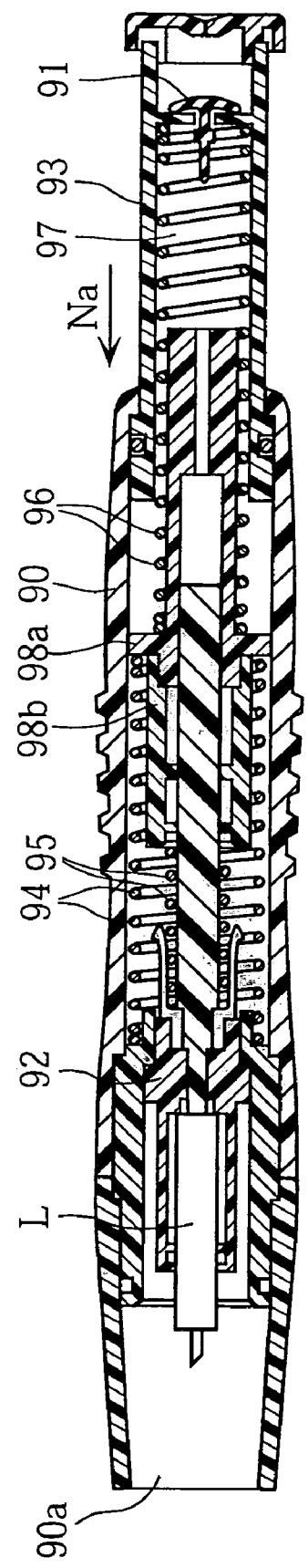
FIG. 31 is a sectional view of a conventional lancing device.

Alternatively to coil springs, leaf spring 17b' may be used as shown in FIG. 30, so that the elastic force from the leaf spring 17b' is used to pull the needle 10b of the lancet 10 once the puncture is made. The leaf spring 17b' may be integral with the cover 20GB, or may be formed separately from the cover 20GB and then integrated with the cover 20GB.

The pump mechanism according to the present invention is not limited to those provided by combination of the cylinder and the plunger, but can include the diaphragm type and other types of pump mechanisms. The drive mechanism for the lancet holder (moving body) according to the present invention can be anything as long as the lancet holder (moving body) can be moved forward toward the front end, and therefore can have mechanisms different from the one used in the embodiments.

The invention claimed is:

1. A lancing device incorporating a vacuum generating mechanism, comprising: a housing having a first housing space; a moving body movable relatively to the housing in the first housing space for forward movement of a needle; a driving mechanism for forward movement of the moving body; a hollow pressing portion at a front end of the housing for contact with a part where a puncture is to be made; and a latch mechanism for latching the moving portion;

wherein the driving mechanism includes:

an elastic portion for urging the moving body in the forward direction; a lancing operation member having at least a part thereof exposed to outside of the housing; and an unlatching portion to act on the latch mechanism for unlatching the moving body upon operation of the lancing operation member;

wherein the latch mechanism includes a first engaging portion provided on the moving body; and a latching member fixed to the housing and having a second engaging portion for engagement with the first engaging portion; and wherein the latching member and the moving body are joined together for defining a second housing space within the first housing space for accommodating the elastic portion.

2. The lancing device according to claim 1, wherein the second housing space also accommodates an elastic portion for reverse movement of the moving body, in series with the elastic portion for forward movement of the moving body, for supplying the moving body with a reverse moving force after the forward movement of the moving body.

3. The lancing device according to claim 1, further comprising a pump mechanism for causing a vacuum to act inside the pressing portion, wherein the pump mechanism is capable of adjusting the vacuum.

4. A lancing device comprising: a housing having a first housing space; a moving holder accommodated in the first housing space for holding a needle, the moving holder being movable relatively to the housing for forward movement of the needle; a driving mechanism for forward movement of the moving holder; and a latch mechanism for latching the moving portion;

wherein the driving mechanism includes: a first elastic member for supplying the moving holder with a forward moving force; and a second elastic member placed in series with the first elastic member for supplying the moving body with a reverse moving force after the forward movement of the moving body; and wherein the latch mechanism includes a latching member for latching the moving holder at a predetermined position relative to the housing in the first housing space, the latching member being separably joined to the moving holder to define a second housing space within the first housing space for accommodating the first and second elastic members in series with each other.

5. The lancing device according to claim 4, wherein a portion of the moving holder forms a first cylinder half, a portion of the latching member forming a second cylinder half, the first and second cylinder halves providing a full cylinder when joined together.

6. The lancing device according to claim 5, wherein each of the first and second elastic members comprises a coil spring which is expanded or compressed by the forward and reverse movement of the moving holder.

7. A lancing device incorporating a vacuum generating mechanism, comprising: a housing; a moving body movable relatively to the housing for forward movement of a needle; a driving mechanism for forward movement of the moving body; a hollow pressing portion at a front end of the housing for contact with a part where a puncture is to be made; and a pump mechanism capable of causing a vacuum to act inside the pressing portion, wherein the pump mechanism includes: a moving portion capable of reciprocating in a first direction and a second direction away from the first direction; and an elastic force generating portion storing an elastic force by the movement of the moving portion in the first direction and moving the moving portion in the second direction by releasing the elastic force, and wherein the vacuum is generated by the movement of the moving portion in the first direction.

* * * * *